(12) United States Patent
Renga et al.

(10) Patent No.: US 8,871,943 B2
(45) Date of Patent: Oct. 28, 2014

(54) PROCESS FOR THE PREPARATION OF 4-AMINO-5-FLUORO-3-HALO-6-(SUBSTITUTED)PICOLINATES

(71) Applicant: Dow AgroSciences LLC, Indianapolis, IN (US)

(72) Inventors: James M. Renga, Indianapolis, IN (US); Yang Cheng, Midland, MI (US); Joseck M. Muhuhi, Midland, MI (US); David E. Podhorez, Midland, MI (US); Gary A. Roth, Midland, MI (US); Scott P. West, Midland, MI (US); Gregory T. Whiteker, Carmel, IN (US); Yuanming Zhu, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/949,060

(22) Filed: Jul. 23, 2013

(65) Prior Publication Data

US 2014/0031556 A1   Jan. 30, 2014

Related U.S. Application Data

(60) Provisional application No. 61/675,235, filed on Jul. 24, 2012.

(51) Int. Cl.
    *C07D 213/803*   (2006.01)

(52) U.S. Cl.
    CPC .................................. *C07D 213/803* (2013.01)
    USPC ......................................................... 546/310

(58) Field of Classification Search
    None
    See application file for complete search history.

(56) References Cited

U.S. PATENT DOCUMENTS

| | | |
|---|---|---|
| 6,297,197 B1 | 10/2001 | Fields et al. |
| 6,784,137 B2 | 8/2004 | Balko et al. |
| 7,314,849 B2 | 1/2008 | Balko et al. |
| 7,432,227 B2 | 10/2008 | Balko et al. |
| 2012/0190859 A1 | 7/2012 | Zhu et al. |
| 2012/0190860 A1 | 7/2012 | Whiteker et al. |

FOREIGN PATENT DOCUMENTS

WO   03101926   12/2003

OTHER PUBLICATIONS

Fields et al., "Electrophilic fluorination: the aminopyridine dilemma," Tetrahedron Letters, 51(1):79-81 (2010).

*Primary Examiner* — Zinna Northington Davis
(74) *Attorney, Agent, or Firm* — Robert Chang; Jones Day

(57) ABSTRACT

Provided herein are processes for the preparation of 4-amino-5-fluoro-3-halo-6-(substituted)picolinates comprising a step of converting chloropicolinoyl chlorides to fluoropicolinoyl fluorides.

20 Claims, No Drawings

PROCESS FOR THE PREPARATION OF 4-AMINO-5-FLUORO-3-HALO-6-(SUBSTITUTED)PICOLINATES

1. CLAIM OF PRIORITY

Priority is claimed herein to U.S. Provisional Application No. 61/675,235 entitled "Process for the Preparation of 4-Amino-5-Fluoro-3-Halo-6-(Substituted)Picolinates," filed Jul. 24, 2012. The above-referenced application is incorporated by reference herein in its entirety.

2. FIELD

Provided herein are processes for the preparation of 4-amino-5-fluoro-3-halo-6-(substituted)picolinates. More particularly, provided herein are processes for the preparation of 4-amino-5-fluoro-3-halo-6-(substituted)picolinates comprising a step of converting chloropicolinoyl chlorides to fluoropicolinoyl fluorides.

3. BACKGROUND

U.S. Pat. No. 6,297,197 B1 describes inter alia certain 6-(alkoxy or aryloxy)-4-amino-3-chloro-5-fluoropicolinate compounds and their use as herbicides. U.S. Pat. Nos. 6,784,137 B2 and 7,314,849 B2 describe inter alia certain 6-(aryl)-4-amino-3-chloro-5-fluoropicolinate compounds and their use as herbicides. U.S. Pat. No. 7,432,227 B2 describes inter alia certain 6-(alkyl)-4-amino-3-chloro-5-fluoropicolinate compounds and their use as herbicides. Each of these patents describes the manufacture of 4-amino-3-chloro-5-fluoropicolinate starting materials by fluorination of the corresponding 5-unsubstituted pyridines with 1-(chloromethyl)-4-fluoro-1,4-diazoniabicyclo[2.2.2]octane bis(tetrafluoroborate). It would be advantageous to produce 4-amino-5-fluoro-3-halo-6-(substituted)picolinates without having to rely on direct fluorination of the 5-position of the pyridine ring with an expensive fluorinating agent like 1-(chloromethyl)-4-fluoro-1,4-diazoniabicyclo[2.2.2]octane bis(tetrafluoroborate).

U.S. application Ser. No. 13/356,691 describes inter alia processes for the preparation of 4-amino-5-fluoro-3-halo-6-(substituted)picolinates comprising fluorinating a 5-chloropicolinate ester with a source of fluoride ion. U.S. application Ser. No. 13/356,686 describes inter alia processes for the preparation of 4-amino-5-fluoro-3-halo-6-(substituted)picolinates comprising fluorinating a 5-chloro-picolinonitrile compound with a source of fluoride ion. Due to the relatively weak electron withdrawing ability of the ester functional groups, highly reactive fluoride ion source such as CsF is preferred for the fluorination processes disclosed in U.S. application Ser. Nos. 13/356,691 and 13/356,686. When a less reactive fluoride ion source such as KF is used, the fluorination of chloropicolinate compounds may lead to low to moderate yield of the desired product due to incomplete fluorination and decomposition of the starting materials and products under forcing conditions. It would be advantageous to provide improved and more cost efficient methods for the preparation of 4-amino-5-fluoro-3-halo-6-(substituted)picolinates without having to rely on expensive chemical reagents such as CsF.

4. SUMMARY

Provided herein are processes for the preparation of 4-amino-5-fluoro-3-halo-6-(substituted)picolinates. More particularly, provided herein are processes for the preparation of 4-amino-5-fluoro-3-halo-6-(substituted)picolinates comprising a step of converting chloropicolinoyl chlorides to fluoropicolinoyl fluorides.

In one embodiment, provided herein is a process for preparing a compound of Formula (I):

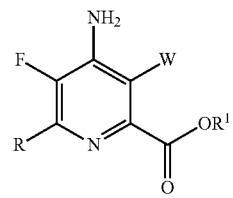

(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

introducing the fluoro substituent to the 5-position of the pyridine structure in Formula (I) by fluorinating a 5-Cl-picolinoyl chloride compound with a source of fluoride ion to form a 5-F-picolinoyl fluoride compound;

introducing the amino substituent to the 4-position of the pyridine structure in Formula (I) by aminating a 4-halo-pyridine compound with an ammonia source;

introducing the W substituent to the 3-position of the pyridine structure in Formula (I) by halogenating a 3-unsubstituted-pyridine compound with a halogen source; and introducing the R substituent to the 6-position of the pyridine structure in Formula (I) by coupling a 6-halo-pyridine compound with a R-Met compound, wherein the R-Met compound is defined herein and elsewhere.

In one embodiment, provided herein is a process for preparing a compound of Formula (I):

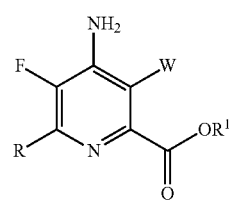

(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

(a) fluorinating a compound of Formula (II):

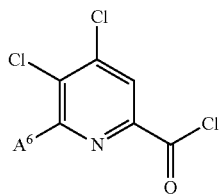

(II)

wherein $A^6$ is halogen or R;
with a source of fluoride ion to form a compound of Formula (III):

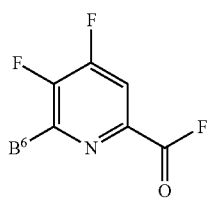

(III);

wherein $B^6$ is F or R;
and transforming the compound of Formula (III) to a compound of Formula (IV):

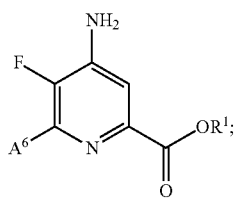

(IV)

(b) halogenating a compound of Formula (IV) with a halogen source to form a compound of Formula (V):

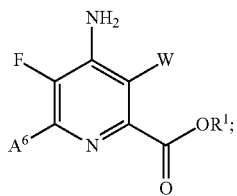

(V)

and
(c) coupling a compound of Formula (VI)

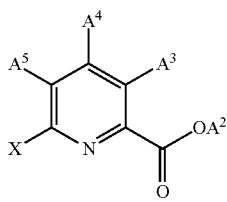

(VI)

wherein
X is Cl, Br, or I;
$A^2$ is hydrogen or $R^1$;
$A^3$ is hydrogen or W;
$A^4$ is Cl, F, $NH_2$, $NHCOCH_3$, or a protected amino group;
$A^5$ is F or Cl;
with a compound of Formula (VII)

R-Met    (VII)

wherein Met is Zn-halide, Zn—R, tri-($C_1$-$C_4$ alkyl)tin, copper, or $B(OR^2)(OR^3)$,
where $R^2$ and $R^3$ are each independently, hydrogen, $C_1$-$C_4$ alkyl, or when taken together form an ethylene or propylene group;
in the presence of a transition metal catalyst to form a compound of Formula (VIII):

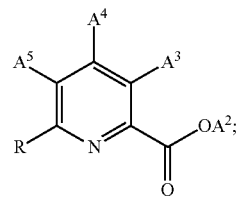

(VIII)

wherein transformation (c) may occur prior to, between, or after transformations (a) and (b).

In one embodiment, provided herein is a process for preparing a compound of Formula (I):

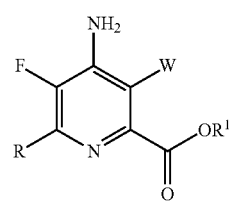

(I)

or a salt, solvate including a hydrate, isotopologue, or polymorph thereof, wherein:
W represents Cl, Br or I;
R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; comprising:
introducing the fluoro substituent to the 5-position of the pyridine structure in Formula (I) by fluorinating a 5-Cl-picolinoyl chloride compound with a source of fluoride ion to form a 5-F-picolinoyl fluoride compound;
introducing the amino substituent to the 4-position of the pyridine structure in Formula (I) by aminating a 4-halo-pyridine compound with an ammonia source;
introducing the W substituent to the 3-position of the pyridine structure in Formula (I) by halogenating a 3-unsubstituted-pyridine compound with a halogen source; and
introducing the R substituent to the 6-position of the pyridine structure in Formula (I) by coupling a 6-halo-pyridine compound with a R-Met compound, wherein the R-Met compound is defined herein and elsewhere.

In one embodiment, provided herein is a process for preparing a compound of Formula (I):

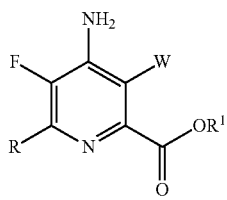
(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

(a) fluorinating a compound of Formula (II):

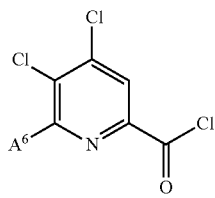
(II)

wherein $A^6$ is halogen or R;

with a source of fluoride ion to form a compound of Formula (III):

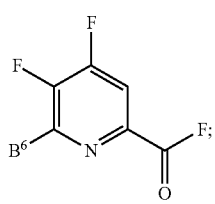
(III)

wherein $B^6$ is F or R;

and transforming the compound of Formula (III) to a compound of Formula (IV):

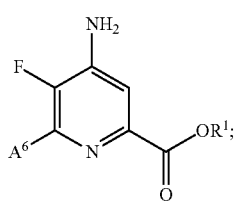
(IV)

(b) halogenating a compound of Formula (IV) with a halogen source to form a compound of Formula (V):

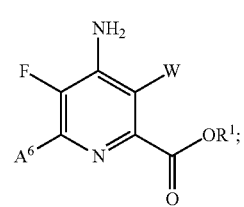
(V)

and (c) coupling a compound of Formula (VI)

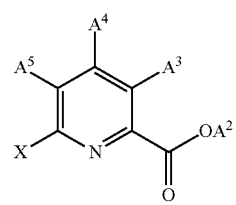
(VI)

wherein

X is Cl, Br, or I;

$A^2$ is hydrogen or $R^1$;

$A^3$ is hydrogen or W;

$A^4$ is Cl, F, $NH_2$, $NHCOCH_3$, or a protected amino group;

$A^5$ is F or Cl;

with a compound of Formula (VII)

$$R\text{-Met} \quad (VII)$$

wherein Met is Zn-halide, Zn—R, tri-($C_1$-$C_4$ alkyl)tin, copper, or $B(OR^2)(OR^3)$, where $R^2$ and $R^3$ are each independently, hydrogen, $C_1$-$C_4$ alkyl, or when taken together form an ethylene or propylene group;

in the presence of a transition metal catalyst to form a compound of Formula (VIII):

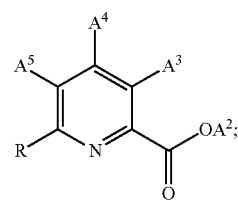
(VIII)

wherein transformation (c) may occur prior to, between, or after transformations (a) and (b).

5. DETAILED DESCRIPTION

5.1 Definition

As used herein and unless otherwise indicated, the term "process(es)" provided herein refers to the methods disclosed herein which are useful for preparing a compound provided herein. Modifications to the methods disclosed herein (e.g., starting materials, reagents, protecting groups, solvents, temperatures, reaction times, purification) are also encompassed by the present disclosure.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive groups or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein, and unless otherwise indicated, a reaction that is "substantially complete" or is driven to "substantial completion" means that the reaction contains more than about 80% by percent yield, in one embodiment more than about 90% by percent yield, in another embodiment more than about 95% by percent yield, and in another embodiment more than about 97% by percent yield of the desired product.

As used herein, and unless otherwise indicated, the term "salt" includes, but is not limited to, salts of acidic or basic groups that may be present in the compounds disclosed herein. Compounds that are basic in nature are capable of forming a wide variety of salts with various inorganic and organic acids. The acids that may be used to prepare salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise indicated, the term "hydrate" means a compound or a salt thereof, that further includes a stoichiometric or non-stoichiometeric amount of water bound by non-covalent intermolecular forces.

As used herein, and unless otherwise indicated, the term "solvate" means a solvate formed from the association of one or more solvent molecules to a compound. The term "solvate" includes hydrates (e.g., mono-hydrate, dihydrate, trihydrate, tetrahydrate, and the like).

As used herein, and unless otherwise indicated, the term "polymorph" means solid crystalline forms of a compound or complex thereof. Different polymorphs of the same compound can exhibit different physical, chemical and/or spectroscopic properties.

The terms "alkyl," "alkenyl" and "alkynyl," as well as derivative terms such as "alkoxy," "acyl," "alkylthio" and "alkylsulfonyl," as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "arylalkyl," as used herein, refers to a phenyl substituted alkyl group having a total of 7 to 11 carbon atoms, such as benzyl (—$CH_2C_6H_5$), 2-methylnaphthyl (—$CH_2C_{10}H_7$) and 1- or 2-phenethyl (—$CH_2CH_2C_6H_5$ or —$CH(CH_3)C_6H_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, $C(O)OC_1$-$C_6$alkyl, or where two adjacent substituents are taken together as —$O(CH_2)_n$—O— wherein n=1 or 2, provided that the substituents are sterically compatible and the rules of chemical bonding and strain energy are satisfied.

Unless specifically limited otherwise, the term "halogen," as well as derivative terms such as "halo," refers to fluorine, chlorine, bromine and iodine.

As used herein, and unless otherwise indicated, the term "amino" or "amino group" means a monovalent group of the formula —$NH_2$, —NH(alkyl), —NH(aryl), —N(alkyl)$_2$, —N(aryl)$_2$ or —N(alkyl)(aryl).

Amino protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (z), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide and 3-nitropyridinesulfenamide (Npys).

As used herein, and unless otherwise indicated, the term "substituted" or "substitution," when used to describe a chemical structure or moiety, refers to a derivative of that structure or moiety wherein one or more of its hydrogen atoms is replaced with a substituent such as, but not limited to: alkyl, alkenyl, alkynyl, and cycloalkyl; alkoxyalkyl; aroyl; deuterium, halo; haloalkyl (e.g., trifluoromethyl); heterocycloalkyl; haloalkoxy (e.g., trifluoromethoxy); hydroxy; alkoxy; cycloalkyloxy; heterocylooxy; oxo; alkanoyl; aryl; heteroaryl (e.g., indolyl, imidazolyl, furyl, thienyl, thiazolyl, pyrrolidyl, pyridyl, and pyrimidyl); arylalkyl; alkylaryl; heteroaryl; heteroarylalkyl; alkylheteroaryl; heterocyclo; heterocycloalkyl-alkyl; aryloxy, alkanoyloxy; amino; alkylamino; arylamino; arylalkylamino; cycloalkylamino; heterocycloamino; mono- and di-substituted amino; alkanoylamino; aroylamino; aralkanoylamino; aminoalkyl; carbamyl (e.g., CONH$_2$); substituted carbamyl (e.g., CONH-alkyl, CONH-aryl, CONH-arylalkyl or instances where there are two substituents on the nitrogen); carbonyl; alkoxycarbonyl; carboxy; cyano; ester; ether; guanidino; nitro; sulfonyl; alkylsulfonyl; arylsulfonyl; arylalkylsulfonyl; sulfonamido (e.g., SO$_2$NH$_2$); substituted sulfonamido; thiol; alkylthio; arylthio; arylalkylthio; cycloalkylthio; heterocyclothio; alkylthiono; arylthiono; and arylalkylthiono. In some embodiments, a substituent itself may be substituted with one or more chemical moieties such as, but not limited to, those described herein.

As used herein, and unless otherwise indicated, the term "about" is used to specify that the values given are approximate. For example, the term "about," where it is used in connection with reaction temperatures, denotes that the temperature deviations within 30%, 25%, 20%, 15%, 10%, or 5% are encompassed by the temperature indicated. Similarly, the term "about," where it is used in connection with reaction time, denotes that the time period deviations within 30%, 25%, 20%, 15%, 10%, or 5% are encompassed by the time period indicated.

The disclosure can be understood more fully by reference to the following detailed description and illustrative examples, which are intended to exemplify non-limiting embodiments.

5.2 Processes

Provided herein are processes for the preparation of 4-amino-5-fluoro-3-halo-6-(substituted)picolinates. More particularly, provided herein are processes for the preparation of 4-amino-5-fluoro-3-halo-6-(substituted)picolinates comprising a step of converting chloropicolinoyl chlorides to fluoropicolinoyl fluorides.

In one embodiment, provided herein is a process for preparing a compound of Formula (I):

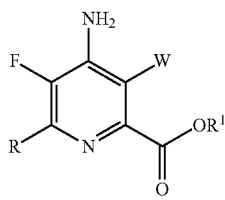

(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

introducing the fluoro substituent to the 5-position of the pyridine structure in Formula (I) by fluorinating a 5-Cl-picolinoyl chloride compound with a source of fluoride ion to form a 5-F-picolinoyl fluoride compound;

introducing the amino substituent to the 4-position of the pyridine structure in Formula (I) by aminating a 4-halo-pyridine compound with an ammonia source;

introducing the W substituent to the 3-position of the pyridine structure in Formula (I) by halogenating a 3-unsubstituted-pyridine compound with a halogen source; and introducing the R substituent to the 6-position of the pyridine structure in Formula (I) by coupling a 6-halo-pyridine compound with a R-Met compound, wherein the R-Met compound is defined herein and elsewhere.

In one embodiment, R is phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy. In one embodiment, R is 4-substituted phenyl, 2,4-disubstituted phenyl, 2,3,4-trisubstituted phenyl, 2,4,5-trisubstituted phenyl, and 2,3,4,6-tetrasubstituted phenyl, wherein each substituent is independently selected from halogen, $C_1$-$C_4$ alkyl, $C_1$-$C_4$ haloalkyl, $C_1$-$C_4$ alkoxy or $C_1$-$C_4$ haloalkoxy.

In one embodiment, provided herein is a process for preparing a compound of Formula (I):

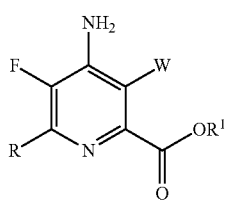

(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

(a) fluorinating a compound of Formula (II):

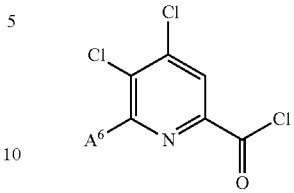

(II)

wherein $A^6$ is halogen or R;
with a source of fluoride ion to form a compound of Formula (III):

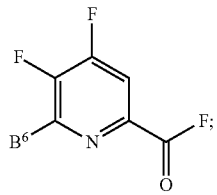

(III)

wherein $B^6$ is F or R;
and transforming the compound of Formula (III) to a compound of Formula (IV):

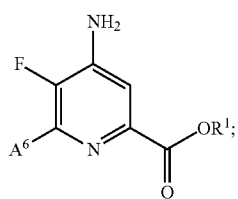

(IV)

(b) halogenating a compound of Formula (IV) with a halogen source to form a compound of Formula (V):

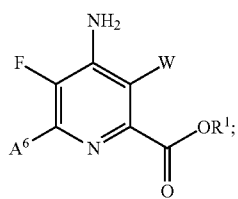

(V)

and
(c) coupling a compound of Formula (VI)

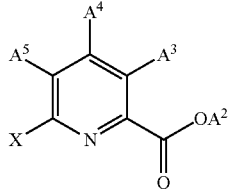

(VI)

wherein
X is Cl, Br, or I;
$A^2$ is hydrogen or $R^1$;
$A^3$ is hydrogen or W;
$A^4$ is Cl, F, $NH_2$, $NHCOCH_3$, or a protected amino group;
$A^5$ is F or Cl;
with a compound of Formula (VII)

R-Met (VII)

wherein Met is Zn-halide, Zn—R, tri-($C_1$-$C_4$ alkyl)tin, copper, or $B(OR^2)(OR^3)$,
where $R^2$ and $R^3$ are each independently, hydrogen, $C_1$-$C_4$ alkyl, or when taken together form an ethylene or propylene group;
in the presence of a transition metal catalyst to form a compound of Formula (VIII):

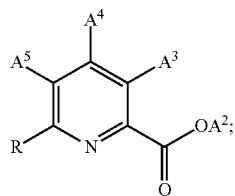

(VIII)

wherein transformation (c) may occur prior to, between, or after transformations (a) and (b).

In one embodiment, provided herein is a process for preparing a compound of Formula (I):

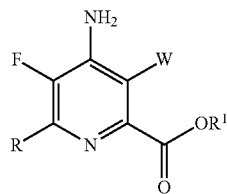

(I)

or a salt, solvate including a hydrate, isotopologue, or polymorph thereof, wherein:
W represents Cl, Br or I;
R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; comprising:
introducing the fluoro substituent to the 5-position of the pyridine structure in Formula (I) by fluorinating a 5-Cl-picolinoyl chloride compound with a source of fluoride ion to form a 5-F-picolinoyl fluoride compound;
introducing the amino substituent to the 4-position of the pyridine structure in Formula (I) by aminating a 4-halo-pyridine compound with an ammonia source;
introducing the W substituent to the 3-position of the pyridine structure in Formula (I) by halogenating a 3-unsubstituted-pyridine compound with a halogen source; and
introducing the R substituent to the 6-position of the pyridine structure in Formula (I) by coupling a 6-halo-pyridine compound with a R-Met compound, wherein the R-Met compound is defined herein and elsewhere.

In one embodiment, R is phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy. In one embodiment, R is 4-substituted phenyl, 2,4-disubstituted phenyl, 2,3,4-trisubstituted phenyl, 2,4,5-trisubstituted phenyl, and 2,3,4,6-tetrasubstituted phenyl, wherein each substituent is independently selected from halogen, $C_1$-$C_4$ alkyl, $C_1$-$C_4$ haloalkyl, $C_1$-$C_4$ alkoxy or $C_1$-$C_4$ haloalkoxy.

In one embodiment, provided herein is a process for preparing a compound of Formula (I):

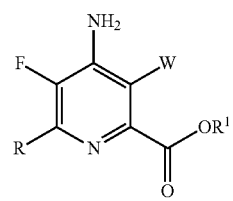

(I)

or a salt, solvate including a hydrate, isotopologue, or polymorph thereof, wherein:
W represents Cl, Br or I;
R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; comprising:
(a) fluorinating a compound of Formula (II):

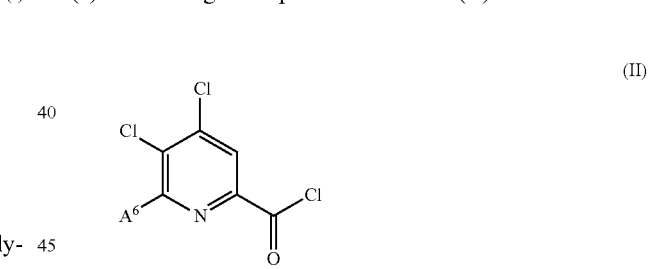

(II)

wherein $A^6$ is halogen or R;
with a source of fluoride ion to form a compound of Formula (III):

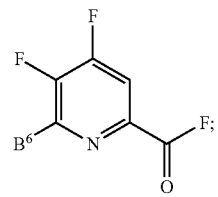

(III)

wherein $B^6$ is F or R;
and transforming the compound of Formula (III) to a compound of Formula (IV):

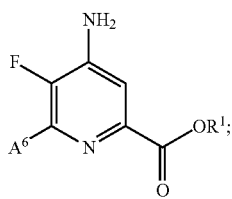

(IV)

(b) halogenating a compound of Formula (IV) with a halogen source to form a compound of Formula (V):

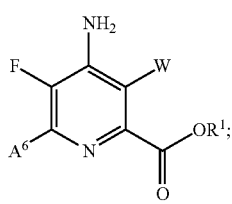

(V)

and
(c) coupling a compound of Formula (VI)

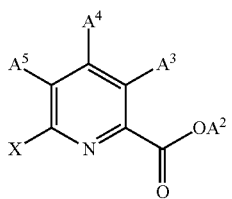

(VI)

wherein
X is Cl, Br, or I;
$A^2$ is hydrogen or $R^1$;
$A^3$ is hydrogen or W;
$A^4$ is Cl, F, $NH_2$, $NHCOCH_3$, or a protected amino group;
$A^5$ is F or Cl;
with a compound of Formula (VII)

R-Met    (VII)

wherein Met is Zn-halide, Zn—R, tri-($C_1$-$C_4$ alkyl)tin, copper, or $B(OR^2)(OR^3)$,
where $R^2$ and $R^3$ are each independently, hydrogen, $C_1$-$C_4$ alkyl, or when taken together form an ethylene or propylene group;
in the presence of a transition metal catalyst to form a compound of Formula (VIII):

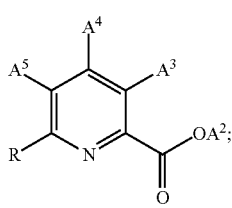

(VIII)

wherein transformation (c) may occur prior to, between, or after transformations (a) and (b).

The order in which the transformation (c) is conducted may be adjusted based on the reaction conditions known in the art. For example, in one embodiment, transformation (c) may occur before transformation (a) and transformation (b). In another embodiment, transformation (c) may occur between transformation (a) and transformation (b). In yet another embodiment, step (c) may occur after transformation (a) and transformation (b).

In one embodiment, provided herein is a process for preparing a compound of Formula (I):

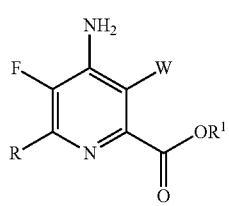

(I)

or a salt, solvate including a hydrate, isotopologue, or polymorph thereof, wherein:

W represents Cl, Br or I;
R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; comprising:

(a) fluorinating a compound of Formula (II):

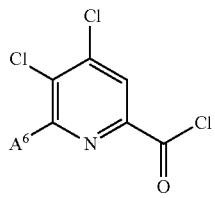

(II)

wherein $A^6$ is halogen or R;
with a source of fluoride ion to form a compound of Formula (III):

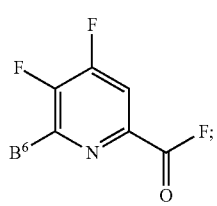

(III)

wherein $B^6$ is F or R;
and transforming the compound of Formula (III) to a compound of Formula (IV):

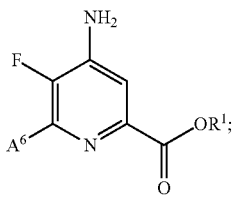

(b) halogenating a compound of Formula (IV) with a halogen source to form a compound of Formula (V):

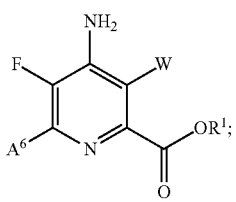

and
(c) coupling a compound of Formula (VI)

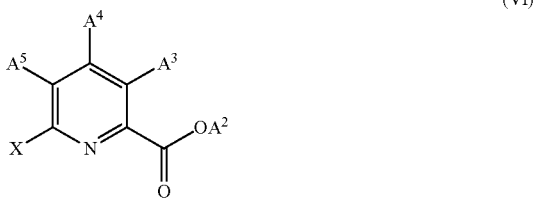

wherein
X is Cl, Br, or I;
$A^2$ is hydrogen or $R^1$;
$A^3$ is hydrogen or W;
$A^4$ is Cl, F, $NH_2$, $NHCOCH_3$, or a protected amino group;
$A^5$ is F or Cl;
with a compound of Formula (VII)

R—Met (VII)

wherein Met is Zn-halide, Zn—R, tri-($C_1$-$C_4$ alkyl)tin, copper, or $B(OR^2)(OR^3)$,
where $R^2$ and $R^3$ are each independently, hydrogen, $C_1$-$C_4$ alkyl, or when taken together form an ethylene or propylene group;
in the presence of a transition metal catalyst to form a compound of Formula (VIII):

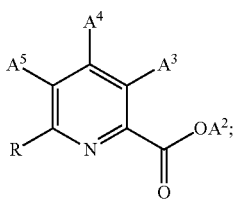

wherein the transformations occur in the following order:
(i) transformation (a) occurs before transformation (b), which occurs before transformation (c);

(ii) transformation (a) occurs before transformation (c), which occurs before transformation (b); or
(iii) transformation (c) occurs before transformation (a), which occurs before transformation (b).

In one embodiment, provided herein is a process for preparing a compound of Formula (I):

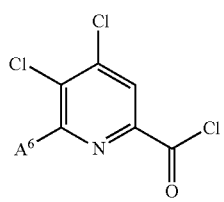

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

(a) fluorinating a compound of Formula (II):

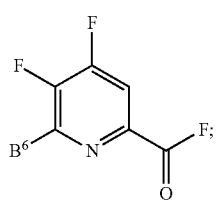

wherein $A^6$ is halogen or R;
with a source of fluoride ion to form a compound of Formula (III):

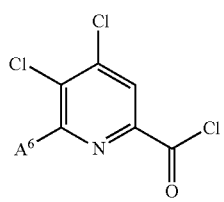

wherein $B^6$ is F or R;

and transforming the compound of Formula (III) to a compound of Formula (IV):

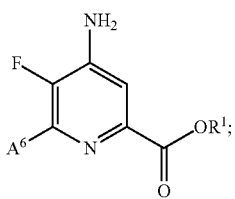

(IV)

(b) halogenating a compound of Formula (IV) with a halogen source to form a compound of Formula (V):

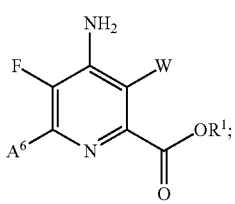

(V)

and
(c) coupling a compound of Formula (VI)

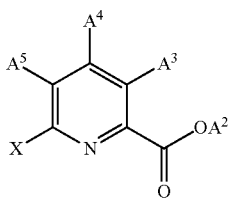

(VI)

wherein
X is Cl, Br, or I;
$A^2$ is hydrogen or $R^1$;
$A^3$ is hydrogen or W;
$A^4$ is Cl, F, $NH_2$, $NHCOCH_3$, or a protected amino group;
$A^5$ is F or Cl;
with a compound of Formula (VII)

R-Met  (VII)

wherein Met is Zn-halide, Zn—R, tri-($C_1$-$C_4$ alkyl)tin, copper, or $B(OR^2)(OR^3)$,
where $R^2$ and $R^3$ are each independently, hydrogen, $C_1$-$C_4$ alkyl, or when taken together form an ethylene or propylene group;
in the presence of a transition metal catalyst to form a compound of Formula (VIII):

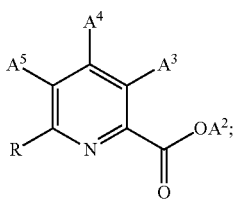

(VIII)

wherein the transformations occur in the following order:
(i) transformation (a) occurs before transformation (b), which occurs before transformation (c);

(ii) transformation (a) occurs before transformation (c), which occurs before transformation (b); or
(iii) transformation (c) occurs before transformation (a), which occurs before transformation (b).

The processes provided herein may further comprise additional steps involving the manipulation of functional groups on the pyridine structure of the formulas provided herein (e.g., esterification and/or hydrolysis of the carboxylic acid group in the 2-position of the pyridine structure, protection and/or deprotection of the amino group in the 4-position of the pyridine structure; and halogen exchange in the 6-position of the pyridine structure). Such manipulation of functional groups may occur under any suitable conditions known in the art. See, e.g., U.S. application Ser. Nos. 13/356,691 and 13/356,686, the entireties of which are incorporated herein by reference.

In one embodiment of fluorinating a compound of Formula (II) to form a compound of Formula (III), $A^6$ is halogen and $B^6$ is F. In one embodiment of fluorinating a compound of Formula (II) to form a compound of Formula (III), $A^6$ is $C^1$ and $B^6$ is F. In another embodiment of fluorinating a compound of Formula (II) to form a compound of Formula (III), both $A^6$ and $B^6$ are R.

The transformation of a compound of Formula (III) to a compound of Formula (IV) may comprise multiple steps such as, but not limited to, esterification at the 2-position of the pyridine structure, amination at the 4-position of the pyridine structure, and exchanging the fluoro substituent at the 6-position of the pyridine structure with an iodo, bromo, or chloro substituent. The order in which the said steps are conducted is not critical. The said steps may occur under conditions known in the art that are suitable for the transformation.

In one embodiment, exemplary transformation of a compound of Formula (III) to a compound of Formula (IV) is illustrated in Scheme 1.

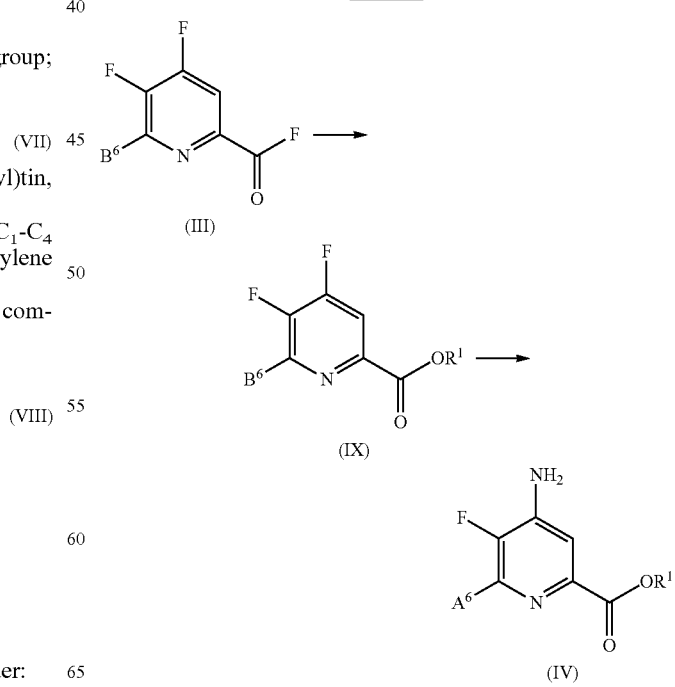

Scheme 1

In one embodiment, the transformation of a compound of Formula (III) to a compound of Formula (IV) comprises: contacting the compound of Formula (III) with an alcohol R¹OH to form a compound of Formula (IX):

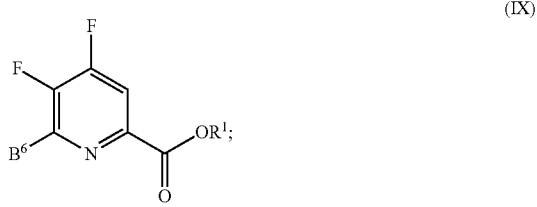

(IX)

and
aminating the compound of Formula (IX) with an ammonia source to form the compound of Formula (IV).

In one embodiment, exemplary transformation of a compound of Formula (III) to a compound of Formula (IV) is illustrated in Scheme 2.

Scheme 2

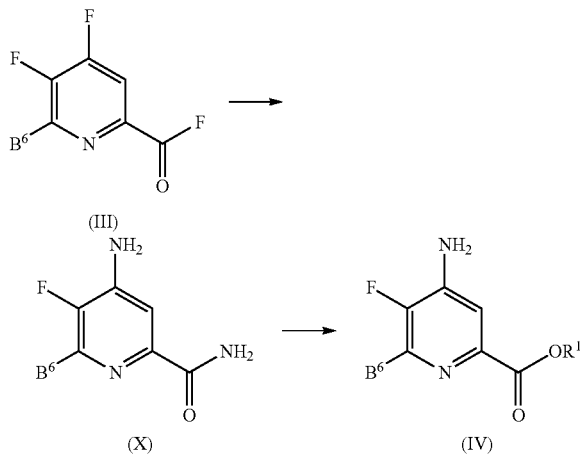

In one embodiment, the transformation of a compound of Formula (III) to a compound of Formula (IV) comprises: contacting the compound of Formula (III) with an ammonia source to form a compound of Formula (X):

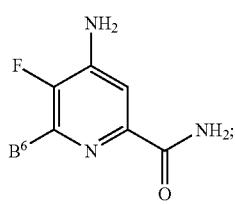

(X)

and
contacting the compound of Formula (X) with an acid HX and an alcohol R¹OH to form the compound of Formula (IV), wherein X is I, Br, or Cl.

In one embodiment of halogenating a compound of Formula (IV) to form a compound of Formula (V), $A^6$ is halogen. In one embodiment of halogenating a compound of Formula (IV) to form a compound of Formula (V), $A^6$ is Cl, Br, or I. In another embodiment of halogenating a compound of Formula (IV) to form a compound of Formula (V), $A^6$ is R.

In one embodiment of coupling a compound of Formula (VI) with R-Met to form a compound of Formula (VIII), $A^2$ is hydrogen. In another embodiment of coupling a compound of Formula (VI) with R-Met to form a compound of Formula (VIII), $A^2$ is R¹.

In one embodiment of coupling a compound of Formula (VI) with R-Met to form a compound of Formula (VIII), $A^4$ is Cl. In another embodiment of coupling a compound of Formula (VI) with R-Met to form a compound of Formula (VIII), $A^4$ is F. In yet another embodiment of coupling a compound of Formula (VI) with R-Met to form a compound of Formula (VIII), $A^4$ is $NH_2$. In yet another embodiment of coupling a compound of Formula (VI) with R-Met to form a compound of Formula (VIII), $A^4$ is $NHCOCH_3$. In yet another embodiment of coupling a compound of Formula (VI) with R-Met to form a compound of Formula (VIII), $A^4$ is NHCOPh, $NHCOCH_2Ph$, NHCOOMe, NHCOOEt, $NHCOOCMe_3$, NHCOOPh or $NHCOOCH_2Ph$.

In some embodiments, the processes provided herein may further comprise protection and deprotection of the amino substituent in the 4-position of the pyridine structure. In some embodiments, the processes provided herein may further comprise protecting the $NH_2$ substituent in the 4-position of the pyridine structure prior to transformation (c); and further comprising a deprotecting step. The suitable amino protection groups are well known to those of ordinary skill in the art. The choice and use of protecting groups and the reaction conditions to install and remove protecting groups are described in T W. Green, *Protective Groups in Organic Synthesis* (Third Ed., Wiley, New York, 1999), which is incorporated herein by reference in its entirety.

In one embodiment, the processes provided herein further comprises protecting the $NH_2$ substituent in the 4-position of the pyridine structure in the Formulas provided herein as $NHCOCH_3$. In one embodiment, the said protection comprises contacting a 4-aminopyridine compound provided herein with $Ac_2O$.

In one embodiment, exemplary transformation of a compound of Formula (VI) to a compound of Formula (VIII) is illustrated in Scheme 3.

Scheme 3

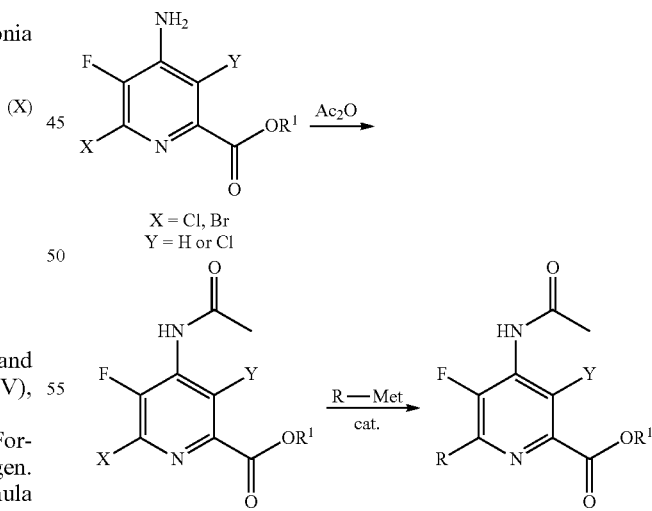

In one embodiment, protection of the amino substituent in the 4-position of the pyridine structure allows the use of lower levels of catalyst in the coupling reactions provided herein between a compound of Formula (VI) and R-Met.

In one embodiment, provided herein is a process as illustrated in Scheme 4.

Scheme 4

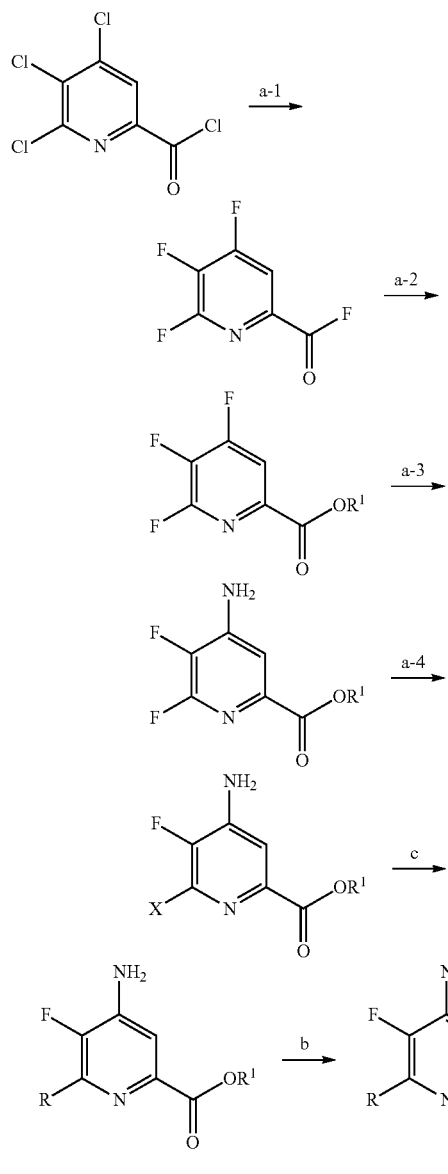

In one embodiment, provided herein is a process for preparing a compound of Formula (I):

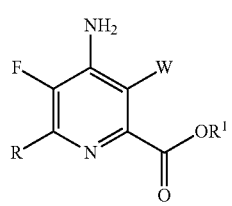

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

transformation (a), which comprises:

(a-1) fluorinating a compound of Formula (A):

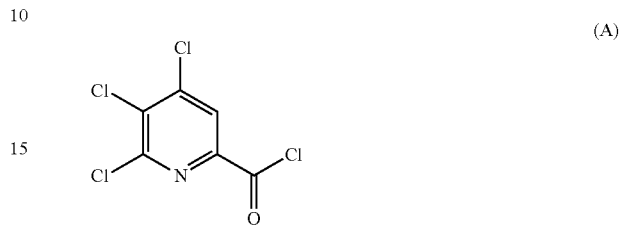

with a source of fluoride ion to form a compound of Formula (B):

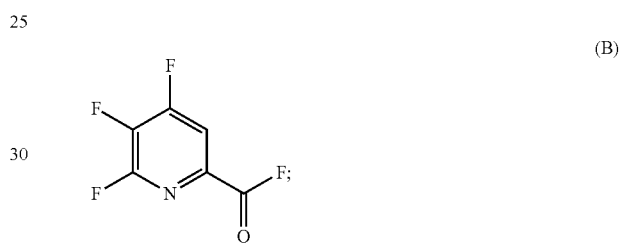

(a-2) contacting the compound of Formula (B) with an alcohol $R^1OH$ to form a compound of Formula (C):

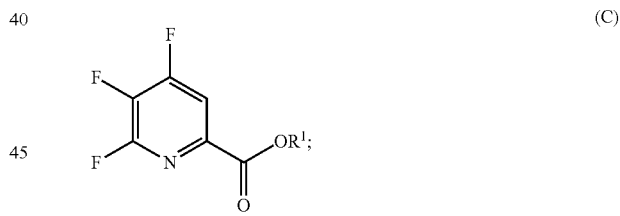

(a-3) aminating the compound of Formula (C) with an ammonia source to form a compound of Formula (D):

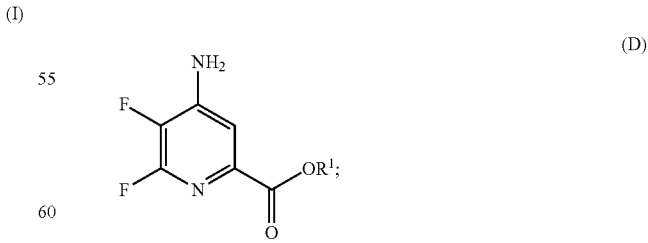

and (a-4) contacting the compound of Formula (D) with an iodide, bromide or chloride source under conditions suitable for halogen exchange to form a compound of Formula (E):

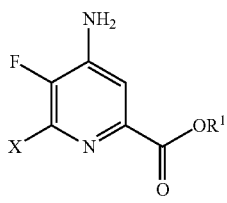

wherein X is Cl, Br, or I;

transformation (c), which comprises:

coupling the compound of Formula (E) with a compound of Formula (F)

R-Met    (F)

wherein Met is Zn-halide, Zn—R, tri-($C_1$-$C_4$ alkyl)tin, copper, or B($OR^2$)($OR^3$), where $R^2$ and $R^3$ are each independently, hydrogen, $C_1$-$C_4$ alkyl, or when taken together form an ethylene or propylene group;

in the presence of a transition metal catalyst to form a compound of Formula (G):

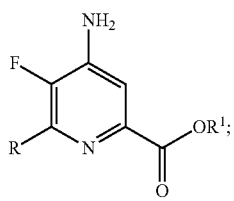

and transformation (b), which comprises:

halogenating the compound of Formula (G) with a halogen source to form a compound of Formula (I).

In one embodiment, provided herein is a process for preparing a compound of Formula (I):

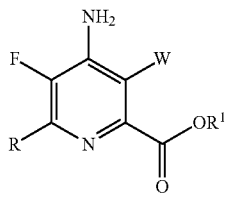

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

transformation (a), which comprises:

(a-1) fluorinating a compound of Formula (A):

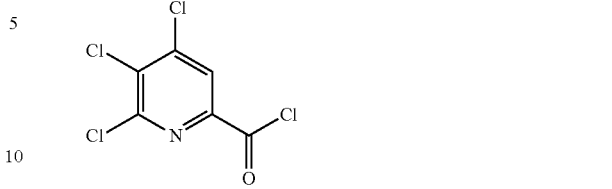

with a source of fluoride ion to form a compound of Formula (B):

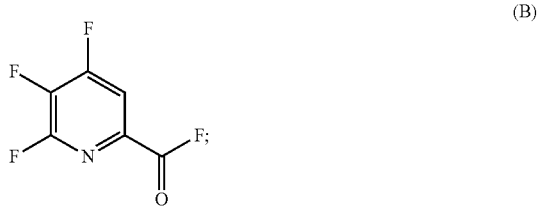 [SMILES: O=C(F)c1cc(F)c(F)c(F)n1]

(a-2) contacting the compound of Formula (B) with an alcohol $R^1OH$ to form a compound of Formula (C):

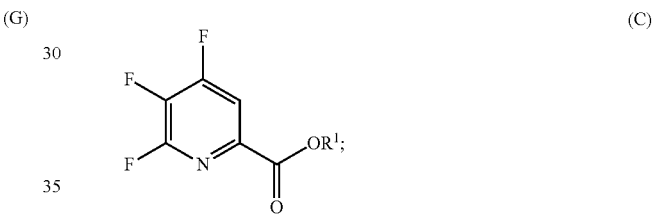

(a-3) aminating the compound of Formula (C) with an ammonia source to form a compound of Formula (D):

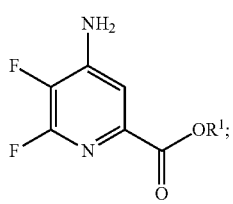

and (a-4) contacting the compound of Formula (D) with an iodide, bromide or chloride source under conditions suitable for halogen exchange to form a compound of Formula (E):

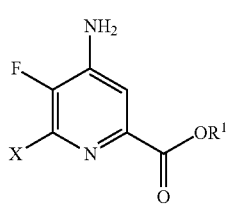

wherein X is Cl, Br, or I;

transformation (c), which comprises:

coupling the compound of Formula (E) with a compound of Formula (F)

R-Met (F)

wherein Met is Zn-halide, Zn—R, tri-($C_1$-$C_4$ alkyl)tin, copper, or B(OR$^2$)(OR$^3$), where $R^2$ and $R^3$ are each independently, hydrogen, $C_1$-$C_4$ alkyl, or when taken together form an ethylene or propylene group;

in the presence of a transition metal catalyst to form a compound of Formula (G):

(G)

and transformation (b), which comprises:

halogenating the compound of Formula (G) with a halogen source to form a compound of Formula (I).

In one embodiment, provided herein is a process as illustrated in Scheme 5.

Scheme 5

In one embodiment, provided herein is a process for preparing a compound of Formula (I):

(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

transformation (a), which comprises:

(a-1) fluorinating a compound of Formula (A):

(A)

with a source of fluoride ion to form a compound of Formula (B):

(B)

(a-2) contacting the compound of Formula (B) with an alcohol R¹OH to form a compound of Formula (C):

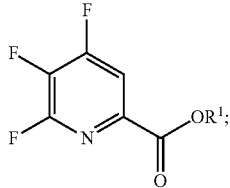

(C)

(a-3) aminating the compound of Formula (C) with an ammonia source to form a compound of Formula (D):

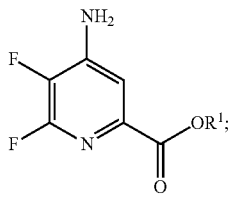

(D)

and
(a-4) contacting the compound of Formula (D) with an iodide, bromide or chloride source under conditions suitable for halogen exchange to form a compound of Formula (E):

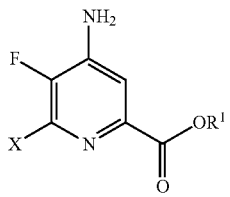

(E)

wherein X is Cl, Br, or I;
transformation (b), which comprises:
halogenating the compound of Formula (E) with a halogen source to form a compound of Formula (H):

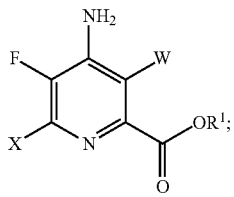

(H)

and
transformation (c), which comprises:
coupling the compound of Formula (H) with a compound of Formula (F)

R-Met    (F)

wherein Met is Zn-halide, Zn—R, tri-($C_1$-$C_4$ alkyl)tin, copper, or B(OR²)(OR³), where R² and R³ are each independently, hydrogen, $C_1$-$C_4$ alkyl, or when taken together form an ethylene or propylene group;

in the presence of a transition metal catalyst to form a compound of Formula (I).

In one embodiment, provided herein is a process for preparing a compound of Formula (I):

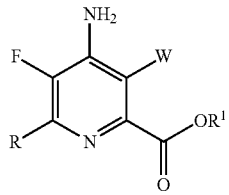

(I)

or a salt, solvate including a hydrate, isotopologue, or polymorph thereof, wherein:
W represents Cl, Br or I;
R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and
R¹ represents $C_1$-$C_{12}$ alkyl or an unsubstituted or substituted $C_7$-$C_{11}$ arylalkyl; comprising:
transformation (a), which comprises:
(a-1) fluorinating a compound of Formula (A):

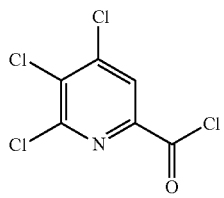

(A)

with a source of fluoride ion to form a compound of Formula (B):

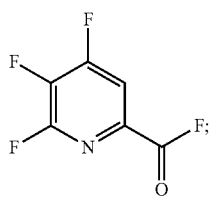

(B)

(a-2) contacting the compound of Formula (B) with an alcohol R¹OH to form a compound of Formula (C):

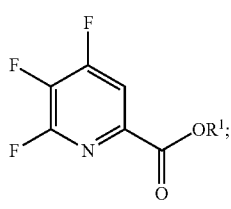

(C)

(a-3) aminating the compound of Formula (C) with an ammonia source to form a compound of Formula (D):

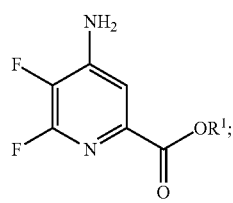

(D)

and (a-4) contacting the compound of Formula (D) with an iodide, bromide or chloride source under conditions suitable for halogen exchange to form a compound of Formula (E):

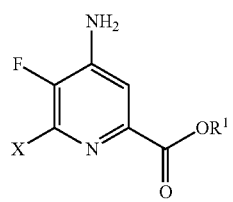

(E)

wherein X is Cl, Br, or I;
transformation (b), which comprises:
halogenating the compound of Formula (E) with a halogen source to form a compound of Formula (H):

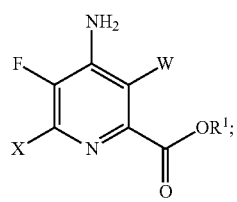

(H)

and
transformation (c), which comprises:
coupling the compound of Formula (H) with a compound of Formula (F)

R-Met    (F)

wherein Met is Zn-halide, Zn—R, tri-($C_1$-$C_4$ alkyl)tin, copper, or B($OR^2$)($OR^3$), where $R^2$ and $R^3$ are each independently, hydrogen, $C_1$-$C_4$ alkyl, or when taken together form an ethylene or propylene group;
in the presence of a transition metal catalyst to form a compound of Formula (I).

In one embodiment, the processes provided herein are illustrated in Scheme 6.

Scheme 6

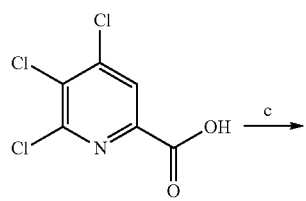

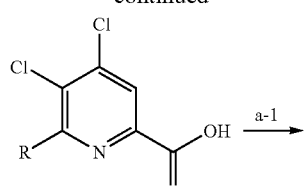

a-1

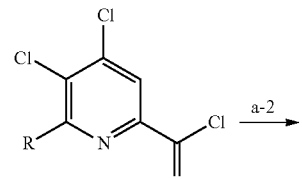

a-2

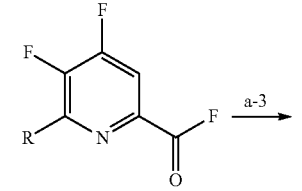

a-3

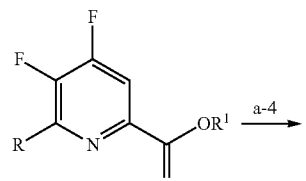

a-4

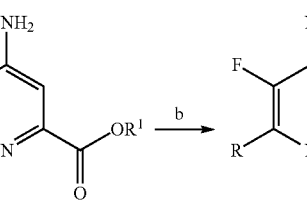

b

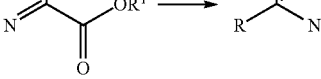

In one embodiment, provided herein is a process for preparing a compound of Formula (I):

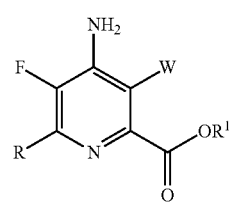

(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

transformation (c), which comprises:
coupling a compound of Formula (J):

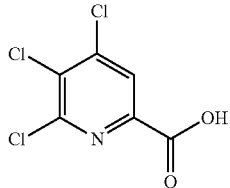
(J)

with a compound of Formula (F)

R-Met    (F)

wherein Met is Zn-halide, Zn—R, tri-($C_1$-$C_4$ alkyl)tin, copper, or B(O$R^2$)(O$R^3$), where $R^2$ and $R^3$ are each independently, hydrogen, $C_1$-$C_4$ alkyl, or when taken together form an ethylene or propylene group;
in the presence of a transition metal catalyst to form a compound of Formula (K):

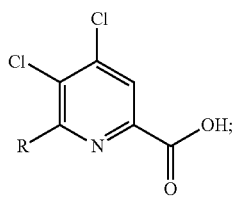
(K)

transformation (a), which comprises:
(a-1) transforming the compound of Formula (K) to a compound of Formula (L):

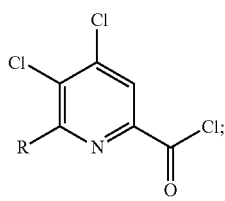
(L)

under conditions suitable for the formation of acid chloride;
(a-2) fluorinating the compound of Formula (L) with a source of fluoride ion to form a compound of Formula (M):

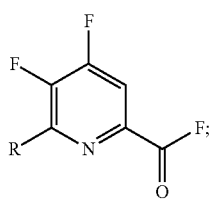
(M)

(a-3) contacting the compound of Formula (M) with an alcohol $R^1$OH to form a compound of Formula (N):

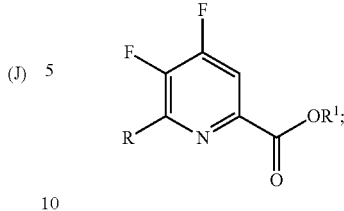
(N)

and
(a-4) aminating the compound of Formula (N) with an ammonia source to form a compound of Formula (O):

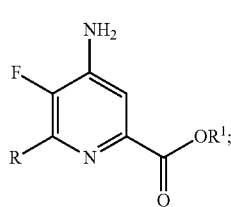
(O)

and
transformation (b), which comprises:
halogenating the compound of Formula (O) with a halogen source to form a compound of Formula (I).
In one embodiment, provided herein is a process for preparing a compound of Formula (I):

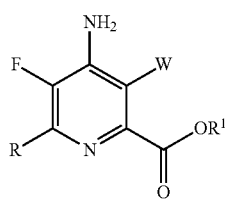
(I)

or a salt, solvate including a hydrate, isotopologue, or polymorph thereof, wherein:
W represents Cl, Br or I;
R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; comprising:
transformation (c), which comprises:
coupling a compound of Formula (J):

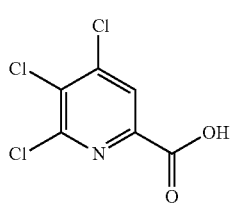
(J)

with a compound of Formula (F)

R-Met    (F)

wherein Met is Zn-halide, Zn—R, tri-($C_1$-$C_4$ alkyl)tin, copper, or B($OR^2$)($OR^3$), where $R^2$ and $R^3$ are each independently, hydrogen, $C_1$-$C_4$ alkyl, or when taken together form an ethylene or propylene group;

in the presence of a transition metal catalyst to form a compound of Formula (K):

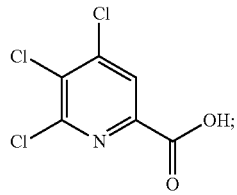
(K)

transformation (a), which comprises:

(a-1) transforming the compound of Formula (K) to a compound of Formula (L):

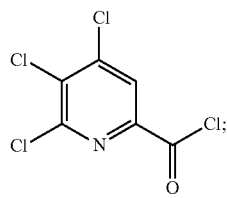
(L)

under conditions suitable for the formation of acid chloride;

(a-2) fluorinating the compound of Formula (L) with a source of fluoride ion to form a compound of Formula (M):

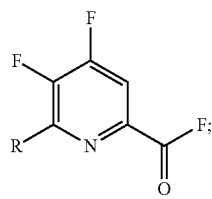
(M)

(a-3) contacting the compound of Formula (M) with an alcohol $R^1OH$ to form a compound of Formula (N):

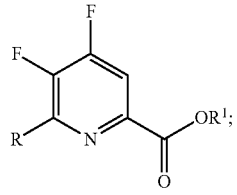
(N)

and (a-4) aminating the compound of Formula (N) with an ammonia source to form a compound of Formula (O):

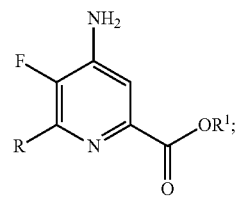
(O)

and transformation (b), which comprises:

halogenating the compound of Formula (O) with a halogen source to form a compound of Formula (I).

In one embodiment, the processes provided herein are illustrated in Scheme 7.

Scheme 7

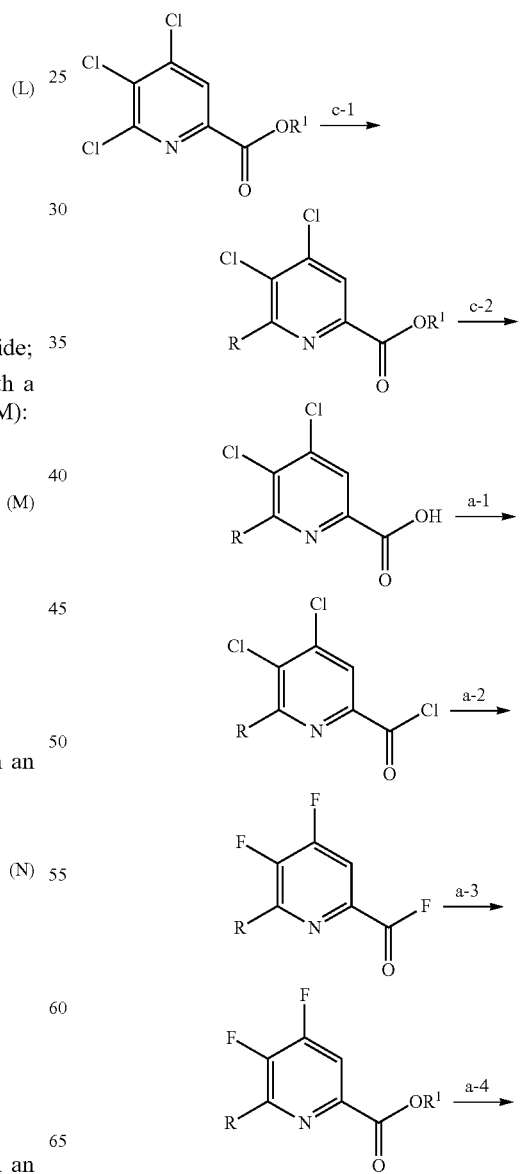

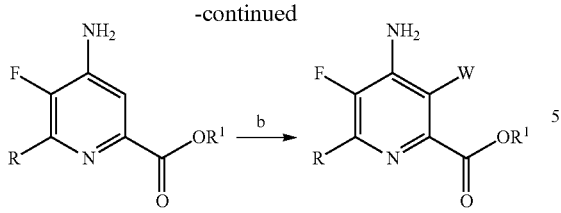

In one embodiment, provided herein is a process for preparing a compound of Formula (I):

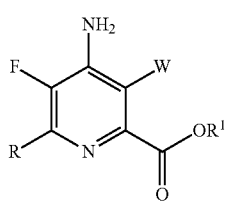

(I)

or a salt, solvate including a hydrate, isotopologue, or polymorph thereof, wherein:
W represents Cl, Br or I;
R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; comprising:
transformation (c), which comprises:
(c-1) coupling a compound of Formula (P):

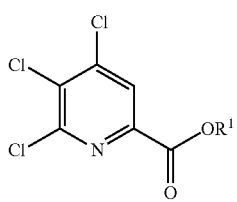

(P)

with a compound of Formula (F)

R-Met  (F)

wherein Met is Zn-halide, Zn—R, tri-($C_1$-$C_4$ alkyl)tin, copper, or B($OR^2$)($OR^3$), where $R^2$ and $R^3$ are each independently, hydrogen, $C_1$-$C_4$ alkyl, or when taken together form an ethylene or propylene group;
in the presence of a transition metal catalyst to form a compound of Formula (Q):

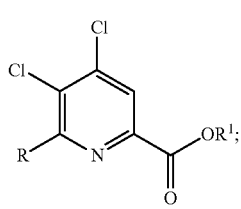

(Q)

and (c-2) hydrolyzing the compound of Formula (Q) to a compound of Formula (K):

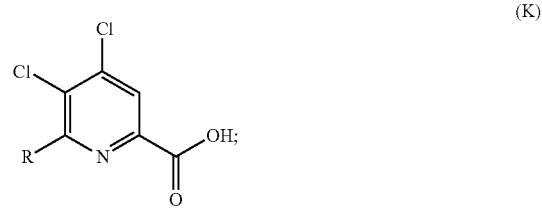

(K)

transformation (a), which comprises:
(a-1) transforming the compound of Formula (K) to a compound of Formula (L):

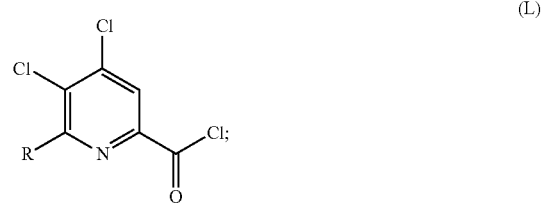

(L)

under conditions suitable for the formation of acid chloride;
(a-2) fluorinating the compound of Formula (L) with a source of fluoride ion to form a compound of Formula (M):

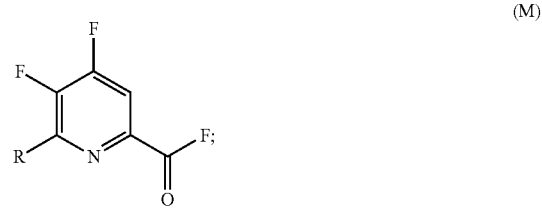

(M)

(a-3) contacting the compound of Formula (M) with an alcohol $R^1$OH to form a compound of Formula (N):

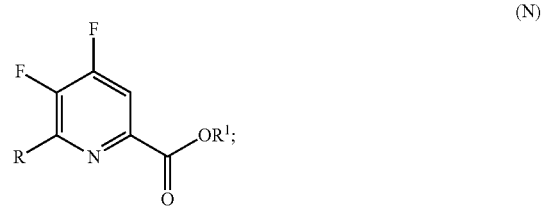

(N)

and (a-4) aminating the compound of Formula (N) with an ammonia source to form a compound of Formula (O):

(O)

and transformation (b), which comprises:

halogenating the compound of Formula (O) with a halogen source to form a compound of Formula (I).

In one embodiment, provided herein is a process for preparing a compound of Formula (I):

(I)

or a salt, solvate including a hydrate, isotopologue, or polymorph thereof, wherein:

W represents Cl, Br or I;

R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; comprising:

transformation (c), which comprises:

(c-1) coupling a compound of Formula (P):

(P)

with a compound of Formula (F)

R-Met  (F)

wherein Met is Zn-halide, Zn—R, tri-($C_1$-$C_4$ alkyl)tin, copper, or $B(OR^2)(OR^3)$, where $R^2$ and $R^3$ are each independently, hydrogen, $C_1$-$C_4$ alkyl, or when taken together form an ethylene or propylene group;

in the presence of a transition metal catalyst to form a compound of Formula (Q):

(Q)

and (c-2) hydrolyzing the compound of Formula (Q) to a compound of Formula (K):

(K)

transformation (a), which comprises:

(a-1) transforming the compound of Formula (K) to a compound of Formula (L):

(L)

under conditions suitable for the formation of acid chloride;

(a-2) fluorinating the compound of Formula (L) with a source of fluoride ion to form a compound of Formula (M):

(M)

(a-3) contacting the compound of Formula (M) with an alcohol $R^1$OH to form a compound of Formula (N):

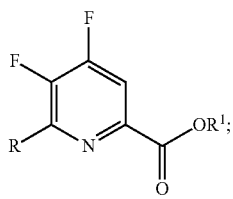

and (a-4) aminating the compound of Formula (N) with an ammonia source to form a compound of Formula (O):

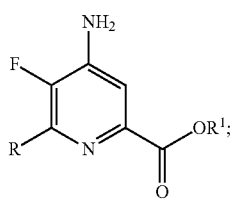

and transformation (b), which comprises:

halogenating the compound of Formula (O) with a halogen source to form a compound of Formula (I).

The chloropicolinoyl chloride compounds (e.g., a compound of Formula (II)) are known compounds, and/or may be prepared from known chloropicolinates using routine techniques known in the art. See, e.g., U.S. Pat. No. 6,784,137 B2. Two exemplary schemes for the preparation of a 6-aryl-picolinoyl chloride are shown below:

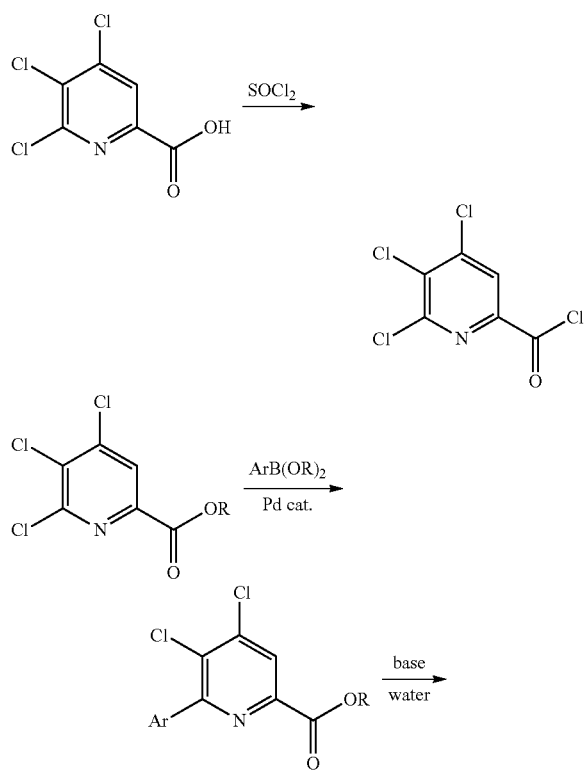

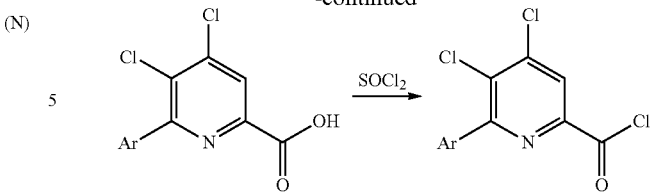

In the fluorine exchange reaction (e.g., transformation of a compound of Formula (II) to a compound of Formula (III)), the fluorinated picolinate is prepared by reacting the corresponding chlorinated picolinate with at least one equivalent of fluoride ion source for each chlorine substituent to be exchanged.

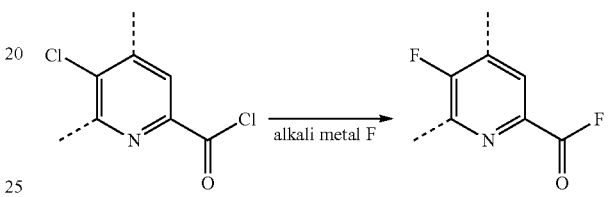

Typical fluoride ion sources include alkali metal fluorides ("M-F"), which include sodium fluoride (NaF), potassium fluoride (KF) and cesium fluoride (CsF). Fluoride salts such as tetrabutylammonium fluoride (n-Bu$_4$NF) may also be used.

In some embodiments, the fluorine exchange reactions are carried out in a solvent or reaction medium such as, acetonitrile, sulfolane, alkyl nitriles, polyethers, or alkyl sulfones, including mixtures thereof. In certain embodiments, the solvent used is an alkyl nitrile or an alkyl sulfone. In certain embodiments, the solvent used is acetonitrile or sulfolane.

Catalysts such as crown ethers or phase transfer agents which are known to increase the rate of fluoride exchange may also be used. In some embodiments, the catalyst is a crown ether, a phosphonium halide, a polyether, a phosphazenium salt, or a tetra-substituted ammonium halide. In certain embodiments, the catalyst is a crown ether, e.g., 18-crown-6.

The temperature at which the fluorine exchange reaction is conducted is not critical but usually is from about 50° C. to about 200° C., and in some embodiments, from about 80° C. to about 140° C. Depending upon which solvent is employed in a particular reaction, the optimum temperature will vary. Generally speaking the lower the temperature the slower the reaction will proceed. The present reactions are typically conducted in the presence of vigorous agitation sufficient to maintain an essentially uniformly dispersed mixture of the reactants.

In conducting the fluorine exchange reaction, neither the rate, nor the order, of addition of the reactants is typically critical. Usually, the solvent and alkali metal fluoride, and optionally, the catalyst, are mixed before the picolinoyl chloride is added to the reaction mixture. A typical reaction generally requires from about 2 to about 100 hours and is usually conducted at ambient atmospheric pressure. In some embodiments, the reaction is conducted at a pressure up to and including 500 psi.

The exact amount of reactants is not critical. In one embodiment, an amount of alkali metal fluoride which will supply at least about an equimolar amount of fluorine atoms based on the number of chlorine atoms to be exchanged in the starting material, i.e., at least an equimolar amount of alkali metal fluoride, is employed.

In the amination, a 4-fluoropicolinate is allowed to react with ammonia to replace the fluorine atom with an amino group.

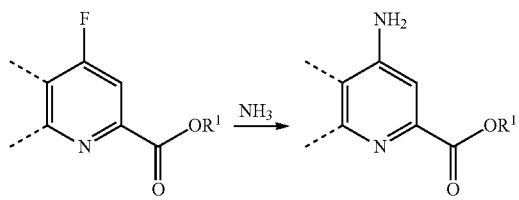

While only a stoichiometric amount of ammonia is required, it is often convenient to use a large excess of ammonia. The reaction is carried out in an inert solvent, in some embodiments, a polar aprotic solvent or reaction medium such as DMSO, NMP, DMF, HMPA or sulfolane. Alternatively, aqueous ammonium hydroxide can be used, with or without use of an organic solvent. The temperature at which the reaction is conducted is not critical but usually is from about 0° C. to about 45° C. and, in some embodiments, from about 10° C. to about 30° C.

In conducting the amination reaction, the 4-fluoropicolinate is dissolved in the solvent, and the ammonia is added to the reaction mixture with cooling. Excess ammonia gas is typically bubbled into the reaction mixture. A typical reaction generally requires from about 0.5 to about 5 hours and is usually conducted at ambient atmospheric pressure. The reaction may be conducted under ammonia pressure up to 30 psi. The reaction may also be conducted using aqueous ammonia.

The amine-containing products or intermediates obtained by any of these processes can be recovered by conventional means, such as evaporation or extraction, and can be purified by standard procedures, such as recrystallization or chromatography. Purification of the amine-containing products or intermediates can also be affected by protonation with an acid to form a salt which is isolated in higher purity by crystallization, precipitation or extraction. A variety of acids, such as hydrochloric acid, hydrobromic acid, nitric acid, acetic acid or sulfuric acid, can be used. In one embodiment, the acid is anhydrous hydrochloric acid. The purified salt is then neutralized with a base to form the neutral amine-containing product or intermediate. Inorganic bases, such as sodium hydroxide, potassium hydroxide, potassium carbonate, sodium carbonate or sodium bicarbonate may be used. In one embodiment, the base is an organic base such as triethylamine. Purification of the amine-containing product or intermediate may be performed in this manner immediately after the amination step, or after subsequent reactions, e.g., halogenation, coupling, have been preformed.

In the halogen (iodine, bromine or chlorine) exchange reaction, the 6-iodinated, 6-brominated or 6-chlorinated picolinate is prepared by reacting the corresponding 6-fluorinated picolinate with at least one equivalent of iodide, bromide or chloride.

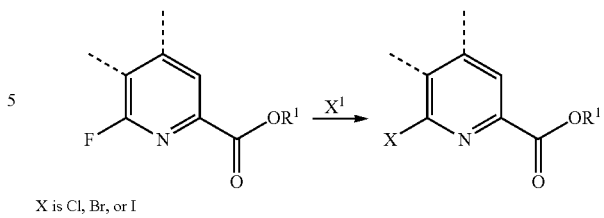

X is Cl, Br, or I

Typically, the halogen exchange reaction is carried out in the presence of a large excess of anhydrous hydrogen iodide (HI), hydrogen bromide (HBr) or hydrogen chloride (HCl). The reaction is typically performed in the absence of water to minimize the formation of by-products. The halogen exchange generally requires from about 5 to about 50 equivalents of HI, HBr or HCl, in some embodiments, from 10 to 20 equivalents. The reaction is carried out in an inert solvent, in some embodiments, a polar solvent such as dioxane or acetic acid. The temperature at which the reaction is conducted is not critical but usually is from about 75° C. to about 150° C. and, in some embodiments, from about 100° C. to about 125° C. The reaction is typically performed in a sealed pressure reactor which is capable of containing HI, HBr or HCl gas. A typical reaction generally requires from about 0.5 to about 5 hours.

In the halogenation reaction, a chlorine, bromine or iodine atom is introduced into the 3-position of the picolinate by reacting the 3-unsubstituted picolinate with a halogen source in an inert solvent.

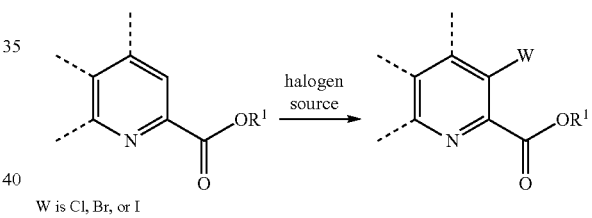

W is Cl, Br, or I

When the halogen atom at the 3-position is Cl, the chlorine source can be chlorine ($Cl_2$) itself or reagents such as sulfuryl chloride, N-chlorosuccinimide or 1,3-dichloro-5,5-dimethylhydantoin. When chlorine or sulfuryl chloride are used, a large excess of chlorinating agent is used. When chlorine gas is used, the reaction is performed in an inert solvent, in some embodiments, a solvent such as dichloromethane, dichloromethane-water or acetic acid. When sulfuryl chloride is used, the reaction can be performed in an inert solvent, such as dichloromethane or in neat sulfuryl chloride. The temperature at which the reaction is conducted is not critical but usually is from about 0° C. to about 45° C. and, in some embodiments, from about 10° C. to about 30° C. A typical reaction generally requires from about 0.5 to about 5 hours. The chlorination reaction is usually conducted at ambient atmospheric pressure.

When the chlorinating agent used is N-chlorosuccinimide or 1,3-dichloro-5,5-dimethylhydantoin, the reaction is carried out using a stoichiometric amount of chlorinating reagent. For chlorinations using 1,3-dichloro-5,5-dimethylhydantoin as the chlorinating agent, both chlorines in the hydantoin are found to react. The reaction is performed in an inert polar solvent, such as DMF or acetonitrile. The temperature at which the reaction is conducted is not critical but usually is from about 20° C. to about 85° C. and, in some embodiments, from about 50° C. to about 80° C. When acetonitrile is used as solvent, it is convenient to carry out the reaction at the reflux temperature. A typical reaction generally requires from about 0.5 to about 5 hours. The chlorination reaction is usually conducted at ambient atmospheric pressure.

When the halogen atom at the 3-position is Br, the bromine source can be bromine ($Br_2$) itself or reagents such as sulfuryl bromide, N-bromosuccinimide or 1,3-dibromo-5,5-dimethylhydantoin. When $Br_2$ is used as the brominating agent, a large excess can be employed, and the reaction is performed in an inert solvent, in some embodiments, a solvent such as dichloromethane, dichloromethane-water or acetic acid. The temperature at which the reaction is conducted is not critical but usually is from about 0° C. to about 45° C. and, in some embodiments, from about 10° C. to about 30° C. A typical reaction generally requires from about 0.5 to about 5 hours. The bromination reaction is usually conducted at ambient atmospheric pressure.

When the brominating agent used is N-bromosuccinimide or 1,3-dibromo-5,5-dimethylhydantoin, the reaction is carried out using a stoichiometric amount of brominating reagent. The reaction is performed in an inert polar solvent, such as DMF or acetonitrile. The temperature at which the reaction is conducted is not critical but usually is from about 20° C. to about 85° C. and, in some embodiments, from about 50° C. to about 80° C. When acetonitrile is used as solvent, it is convenient to carry out the reaction at the reflux temperature. A typical reaction generally requires from about 0.5 to about 5 hours. The bromination reaction is usually conducted at ambient atmospheric pressure.

When the halogen atom at the 3-position is I, the iodine source can be iodine ($I_2$) itself or reagents such as iodine monochloride or N-iodosuccinimide. Periodic acid may be used in conjunction with $I_2$. When $I_2$ is used as the iodinating agent, a large excess of $I_2$ can be employed, and the reaction is performed in an inert solvent, in some embodiments, a solvent such as dichloromethane, dichloromethane-water, methyl alcohol or acetic acid. The temperature at which the reaction is conducted is not critical but usually is from about 0° C. to about 45° C. and, in some embodiments, from about 10° C. to about 30° C. A typical reaction generally requires from about 0.5 to about 5 hours. The iodination reaction is usually conducted at ambient atmospheric pressure.

In the coupling reaction, a 6-iodo, bromo or choropicolinate is reacted with an aryl, alkyl or alkenyl metal compound where the metal is a Zn-halide, Zn—R, tri-($C_1$-$C_4$ alkyl)tin, copper, or $B(OR^2)(OR^3)$, where $R^2$ and $R^3$ are each independently, hydrogen, $C_1$-$C_4$ alkyl, or when taken together form an ethylene or propylene group, in the presence of a transition metal catalyst.

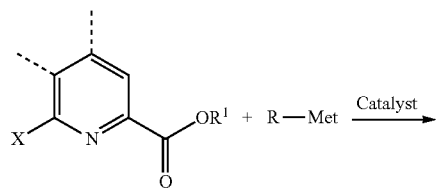

-continued

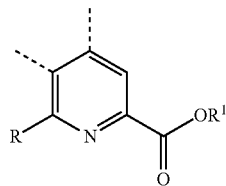

X is Cl, Br, or I

"Catalyst" as used in the coupling reaction is a transition metal catalyst, in particular a palladium catalyst such as palladium diacetate or bis(triphenylphosphine)palladium(II) dichloride, or a nickel catalyst such as nickel(II) acetylacetonate or bis(triphenylphosphine)nickel(II) dichloride. In addition, catalysts can be prepared in situ from metal salts and ligands, such as palladium acetate and triphenylphosphine or nickel(II) chloride and triphenylphosphine. These in situ catalysts can be prepared by prior reaction of metal salt and ligand, followed by addition to the reaction mixture, or by separate addition of the metal salt and ligand directly to the reaction mixture.

Typically, coupling reactions are carried out in the absence of oxygen using an inert gas, such as nitrogen or argon. Techniques used to exclude oxygen from coupling reaction mixtures, such as sparging with inert gas, are well known to those skilled in the art. Examples of such techniques are described in *The Manipulation of Air-Sensitive Compounds*, $2^{nd}$ ed.; Shriver, D. F., Drezdzon, M. A., Eds.; Wiley-Interscience, 1986. Sub-stoichiometric amounts of a catalyst are used, typically from about 0.0001 equivalents to 0.1 equivalents. Additional amounts of ligand may optionally be added to increase catalyst stability and activity. In addition, additives such as $Na_2CO_3$, $K_2CO_3$, KF, CsF, $K_2HPO_4$, $K_3PO_4$ and NaF are typically added to the coupling reaction. The coupling reaction generally requires from about 1 to about 5 equivalents of such additive, in some embodiments, from 1 to 2 equivalents. Water may optionally be added to the coupling reaction to increase the solubility of these additives. The coupling reaction generally requires from 1 to about 3 equivalents of an aryl, alkyl or alkenyl metal compound, in some embodiments, from 1 to 1.5 equivalents. The reaction is carried out in an inert solvent, such as toluene, tetrahydrofuran (THF), dioxane or acetonitrile. The temperature at which the reaction is conducted is not critical but usually is from about 25° C. to about 150° C. and, in some embodiments, from about 50° C. to about 125° C. A typical reaction generally requires from about 0.5 to about 24 hours. No particular order of addition of reactants is typically required. It is often operationally simpler to combine all reactants except the catalyst and then deoxygenate the reaction solution. Following deoxygenation, the catalyst can be added to commence the coupling reaction.

When the Met portion of the aryl, alkyl or alkenyl metal compound is a Zn-halide, Zn—R or copper, protection of reactive functional groups may be necessary. For example, if an amino substituent (—NHR or —$NH_2$) is present, protection of these reactive groups may be required. A variety of groups are known in the art for protection of amino groups from reaction with organometallic reagents. Examples of such protecting groups are described in *Protective Groups in Organic Synthesis*, $3^{rd}$ ed.; Greene, T. W.; Wuts, P. G. M., Eds.; Wiley-Interscience, 1999. The choice of which metal to use in R-Met is influenced by a number of factors, such as cost, stability, reactivity and the need to protect reactive functional groups.

The products obtained by any of these processes can be recovered by conventional means, such as evaporation or extraction, and can be purified by standard procedures, such as recrystallization or chromatography.

All of the combinations of the above embodiments are encompassed by this invention.

6. EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); M (molar); mM (millimolar); µM (micromolar); eq. (equivalent); mmol (millimoles); Hz (Hertz); MHz (megahertz); hr or hrs (hour or hours); min (minutes); and MS (mass spectrometry).

For all of the following examples, unless otherwise specified, standard work-up and purification methods known to those skilled in the art can be utilized. Unless otherwise specified, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

Example 1

4,5,6-Trichloropicolinoyl chloride

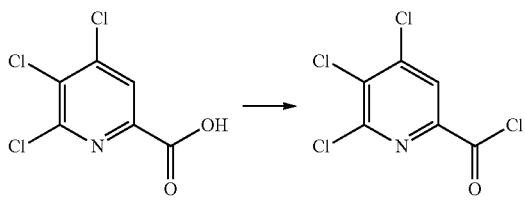 [SMILES: O=C(O)c1cc(Cl)c(Cl)c(Cl)n1 ; O=C(Cl)c1cc(Cl)c(Cl)c(Cl)n1]

A 500 mL three neck round bottom flask with thermowell was fitted with a condenser which vented to a trap and then an aqueous 10% NaOH scrubber, magnetic stir bar, two stoppers and a thermometer. To the vessel was added 4,5,6-trichloropicolinic acid (86 g which contained 8.6 g water, 77.4 g active, 0.32 mol), toluene (160 mL), thionyl chloride (85 mL, 1.12 mol) and DMF (0.3 mL). The slurry was heated to 70-80° C., held there for 7 h and then cooled to room temperature and allowed to stir overnight. Approximately 0.2 mL of the pale yellow solution was placed in a vial and concentrated to a solid under a stream of $N_2$. The solid was treated with a mixture of triethylamine/methanol (0.3 mL/2 mL) and then warmed with a heat gun for ca. 1 min. HPLC analysis indicated that less than 1% of the carboxylic acid remained as compared to the methyl ester derivative. The solution was concentrated on a rotary evaporator leaving a pale yellow solid. The solid was dried (40° C./20 mmHg) for about 1 h providing the title compound (92 g): mp 68-70° C.; $^1$H NMR (CDCl$_3$, 400 MHz) δ 8.12 (s), the solid contained about 4 wt % toluene as determined by integration of the proton signals; $^{13}$C NMR (CDCl$_3$, 101 MHz) δ 167.3, 151.0, 145.82, 145.8, 135.7, 125.5.

Example 2

4,5,6-Trifluoropicolinoyl fluoride

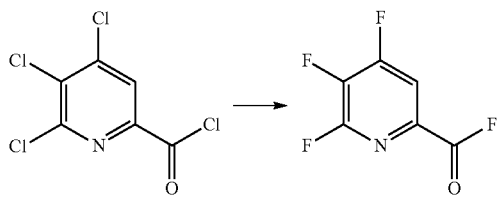 [SMILES: O=C(Cl)c1cc(Cl)c(Cl)c(Cl)n1 ; O=C(F)c1cc(F)c(F)c(F)n1]

A 1-liter three neck round bottom flask was purged with $N_2$ and fitted with a condenser/$N_2$ bubbler, mechanical stirrer and a stopper. To the reactor was added CsF (172 g, 1.13 mol), anhydrous acetonitrile (400 mL), 18-crown-6 (6.0 g, 0.023 mol) and the 4,5,6-trichloropicolinoyl chloride (55 g, 0.23 mol). The mixture was heated to reflux and held there for 20 h. The slurry was cooled to room temperature and the salts filtered under $N_2$ pressure. The salt cake was rinsed with dry acetonitrile (100 mL) to give an amber liquid (372 g). A three neck $N_2$ purged 250 mL round bottom flask with thermowell was fitted with two stoppers, a magnetic stir bar and a vacuum jacketed Vigruex distillation column (15 cm×1 cm) with fraction collector connected to a $N_2$ bubbler. To the vessel was added 140 g of the acetonitrle solution from above. The distillation vessel was heated to 82-85° C. while a clear colorless distillate (acetonitrile) was collected overhead at 80-83° C. When the distillation pot temperature began to rise and the head temperature began to fall the distillation was terminated and allowed to cool to room temperature under $N_2$. The distillation pot residue was transferred to a $N_2$ purged two neck 25 mL round bottom flask. The flask was fitted with a thermometer, magnetic stir bar and the same distillation set up described above. This distillation system could vent to vacuum or $N_2$. Vacuum (ca. 70 mmHg) was established and then heating of the distillation vessel commenced. The product was collected as a clear colorless liquid (6.7 g, by 55-60° C. @ 55-60 mmHg). GC area percent analysis showed the material to be 99.1% pure: $^1$HNMR (CDCl$_3$, 400 MHz) δ 8.08 (ddd, J=8.4, 4.4, 0.4 Hz); MS (GC, 70 eV electron impact) 179 (M$^+$, 100%), 160 (8%), 151 (100%), 132 (80%), 82 (63%); $^{13}$C NMR (101 MHz, CDCl$_3$) δ 157.71 (dt, J=269.0, 6.5 Hz), 152.96 (dd, J=246.1, 13.4 Hz), 152.49 (d, J=348.6 Hz), 138.69 (ddd, J=275.3, 30.2, 12.9 Hz), 135.44 (dddd, J=74.6, 15.1, 7.8 Hz), 117.00 (dt, J=18.2, 4.2 Hz).

In another embodiment, after the filtration and salt cake wash, 366 g of amber solution was obtained. Area percent GC analysis indicated the mixture was 86.4% 4,5,6-trifluoropicolinoyl fluoride and 13.6% 18-C-6. An internal standard GC analysis method was developed using dimethyl phthalate as the internal standard and the material prepared above as the pure component. GC assay of the amber solution indicated it was 9.8 wt. % product which correlated to a yield of 89%.

Example 3

Isopropyl 4,5,6-trifluoropicolinate (via the CsF route)

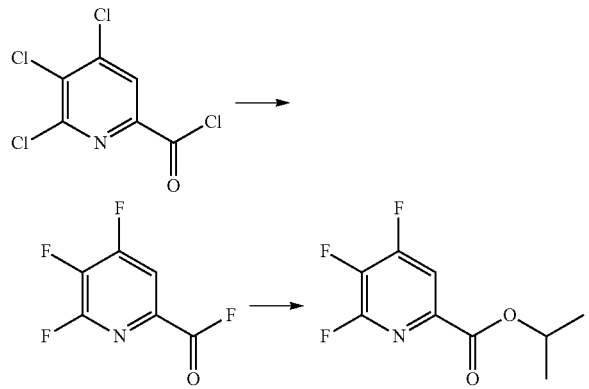

Into a 250 mL 3-necked flask equipped with a mechanical stirrer and a condenser was added 4,5,6-trichloropicolinoyl chloride (23.3 g, 95 mmol), CsF (72.2 g, 475 mmol), 18-crown-6 (2.5 g, 9.5 mmol) and anhydrous acetonitrile (150 mL). The reaction was blanketed with nitrogen, and the mixture was heated at reflux with vigorous stirring for 22 hours. A sample was taken and analyzed by GC. The results showed that the reaction was not complete, therefore additional CsF (14.43 g, 95 mmol) was added, and the mixture was heated at reflux for an additional 24 hours at which time the reaction was deemed complete. Then 6.28 g (104.5 mmol) of anhydrous 2-propanol and 9.61 g (95 mmol) of anhydrous triethyl amine were added to the flask dropwise at 6° C. The mixture was stirred for 5-6 hours at room temperature. The reaction was stopped when GC showed no starting 4,5,6-trifluoropicolinoyl fluoride was left in the mixture. The salts were removed by filtration and washed with some acetonitrile. After removing acetonitrile with a rotary evaporator, the wet product paste was re-dissolved in ethyl ether. The mixture was washed with water and dried over MgSO$_4$. Most of ethyl ether was removed with a rotary evaporator. The concentrated crude product mixture in ethyl ether was filtered through a bed of silica gel, and eluted with some ethyl ether. After stripping away the solvent on a rotary evaporator, 17.52 g (84% yield, 94% HPLC purity) of isopropyl 4,5,6-trifluoropicolinate was obtained $^1$H NMR (CDCl$_3$, 300 MHz) δ 7.90 (ddd, 1H, J=9 Hz, 5 Hz, 1 Hz), 5.30 (m, 1H, J=6 Hz), 1.41 (d, 6H, J=6 Hz); $^{13}$C NMR (CDCl$_3$, 75 MHz, $^1$H decoupled) δ 161.2 (d, J=4 Hz), 157.2 (ddd, J=265 Hz, 9 Hz, 6 Hz), 152.1 (ddd, J=241 Hz, 12 Hz, 5 Hz), 140.9 (m), 136.8 (ddd, J=269 Hz, 30 Hz, 13 Hz), 113.6 (m), 70.4 (s), 21.3 (s).

Example 4

Isopropyl 4,5,6-trifluoropicolinate (via the KF route)

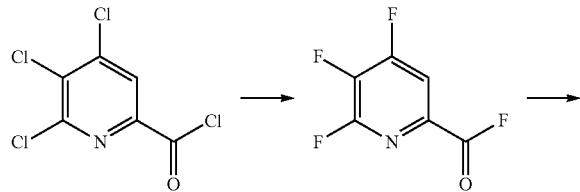
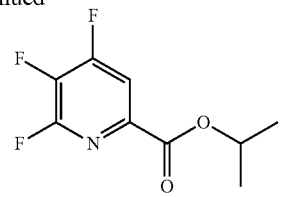

A 100 mL Parr reactor (Hastelloy C construction) was cleaned, dried and leak tested under nitrogen. To this vessel was added 3.673 g (15 mmol) of 4,5,6-trichloropicolinoyl chloride, 7.844 g (135 mmol) of KF, 0.396 g (1.5 mmol) of 18-crown-6 and 40 mL of anhydrous acetonitrile. The entire system was purged with nitrogen. The reaction mixture was stirred at 135° C. for 22 hours, and then was allowed to cool to below 45° C. The system was slowly vented. A sample was taken and analyzed by GC, GC-MS and NMR. GC indicated that the reaction was complete. EIMS m/z=179 (M$^+$, 96%), 160 (11%), 151 (100%), 132 (79%), 82 (73%); $^{19}$F NMR (376 MHz, CD$_3$CN) δ 15.68 (t, J=3.4 Hz), -82.55 (t, J=23.3 Hz), -119.60--119.82 (m), -154.95 (dd, J=24.3, 17.3 Hz). Anhydrous 2-propanol (1.517 g, 25 mmol) and Et$_3$N (1.518, 15 mmol) were slowly added to above reaction mixture in the Parr reactor at 5-10° C. The mixture was stirred at room temperature overnight, and then discharged from the reactor. The salts were removed by filtration and washed with some acetonitrile. The in-pot yield was 77% (GC) as determined by using purified isopropyl 4,5,6-trifluoropicolinate (purity=97 LC area % and 98 GC area %) as a standard and di-propyl-phthalate as a reference. EIMS m/z=178 (M$^+$, 40%), 160 (100%), 132 (69%), 82 (22%), 43 (35%).

Example 5

Isopropyl 4-amino-5,6-difluoropicolinate

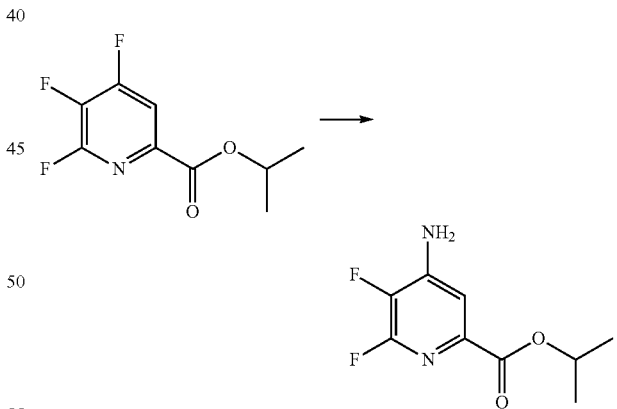

Isopropyl 4,5,6-trifluoropicolinate (17.52 g, 80 mmol) was dissolved in NMP (175 g) in a 500 mL flask equipped with a stirring bar. The mixture was blanketed with nitrogen and then ammonium hydroxide (10.70 g 176 mmol, 28% in water) was added to the flask dropwise at room temperature, and the reaction was stirred overnight. To the reaction was added water (190 mL) and the resulting slurry was cooled in an ice bath and stirred for 5 hours. The solid was collected by filtration and the cake washed with water. Vacuum drying provided the isopropyl 4-amino-5,6-difluoropicolinate as an off-white solid (11.7 g, 68% yield, 96% HPLC purity): mp 167-168° C.;

$^1$H NMR (THF-d$_8$, 300 MHz) δ 7.25 (d, 1H, J=6 Hz), 6.07 (s, 2H), 5.01 (m, 1H, J=6 Hz), 1.20 (d, 6H, J=6.3 Hz); $^{13}$C NMR (THF-d$_8$, 75 MHz, $^1$H decoupled) δ 162.9 (s), 151.5 (dd, J=228 Hz, 12 Hz), 146.1 (dd, J=9 Hz, 6 Hz), 140.4 (dd, J=17 Hz, 5 Hz), 134.5 (dd, J=251 Hz, 32 Hz), 111.9 (m), 68.4 (s), 21.0 (s).

Example 6

Isopropyl 4-amino-6-chloro-5-fluoropicolinate

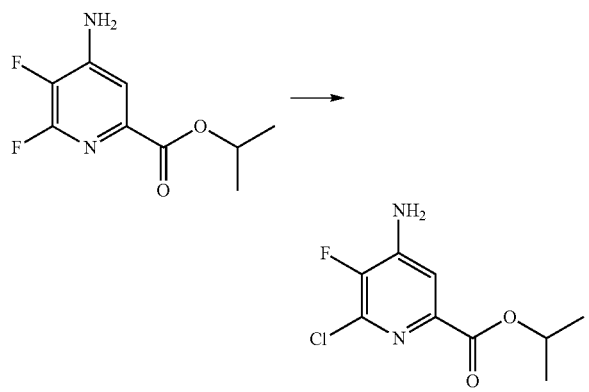

A 100 mL Parr reactor (Hastelloy C construction) was cleaned, dried, and leak tested under nitrogen. To the vessel was charged 1.081 g (5 mmol) of isopropyl 4-amino-5,6-difluoropicolinate and 50 mL of HCl (1 M in acetic acid) (50 mmol). The entire system was purged with nitrogen. The reaction mixture was stirred at 110° C. for 3 hours, and then was allowed to cool to below 50° C. The system was slowly vented and purged with nitrogen. The vent line was dipped into a Na$_2$CO$_3$/water solution. The reaction mixture was concentrated to almost dryness under a flow of nitrogen overnight. A sample was taken and subjected to LC-MS analysis. The results indicated that there were 4 major components in this reaction mixture: isopropyl 4-amino-6-chloro-5-fluoropicolinate (46 area %), isopropyl 4-acetamido-6-chloro-5-fluoropicolinate (33 area %), 4-acetamido-6-chloro-5-fluoropicolinic acid (10 area %) and 4-amino-6-chloro-5-fluoropicolinic acid (7 area %).

Then 50 mL of anhydrous 2-propanol along with 6 drops of concentrated H$_2$SO$_4$ was added to the reactor. The mixture was stirred at 100° C. for 22 hours. After cooling to room temperature, the mixture was discharged from the reactor. The excess of 2-propanol was removed with a rotary evaporator. The solid paste was dissolved in ethyl acetate. The ethyl acetate mixture was first treated with Na$_2$CO$_3$/water solution, then washed with water and dried over MgSO$_4$. The solvent was removed with a rotary evaporator providing crude product (1.00 g, LC purity=90%). After re-crystallization from 2-propanol, white solid product was obtained (0.7 g, LC purity=98%, yield=60%). $^1$H NMR (400 MHz, THF-d$_8$) δ 7.44 (d, J=6.1 Hz, 1H), 6.16 (s, 2H), 5.17 (hept, J=6.3 Hz, 1H), 1.35 (d, J=6.3 Hz, 6H); $^{13}$C NMR (101 MHz, THF-d$_8$) δ 162.97 (s), 145.46 (s), 144.47 (d, J=11.8 Hz), 143.64 (d, J=5.2 Hz), 142.93 (s), 137.06 (d, J=16.4 Hz), 112.57 (d, J=4.0 Hz), 68.51 (s), 21.02 (s); $^{19}$F NMR (376 MHz, THF-d$_8$) δ −143.12 (s).

Example 7

Methyl 4-amino-6-bromo-5-fluoropicolinate

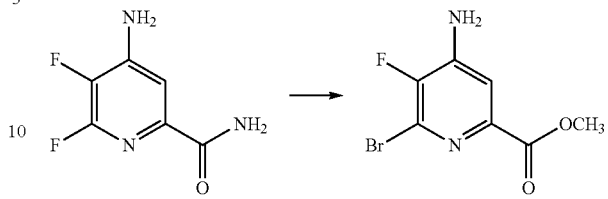

The 100 mL Parr reactor (Hastelloy C construction) was cleaned, dried, and leak tested under nitrogen. 4-Amino-5,6-difluoropicolinamide (5.196 g, 30 mmol), and HBr (54 mL, 300 mmol, 33 wt % in acetic acid) were charged to the Parr reactor. The entire system was purged with nitrogen. The reaction mixture was stirred at 115° C. for 3 hours, and then was allowed to cool to below 45° C. The system was slowly vented and purged with nitrogen. The vent line was dipped into a Na$_2$CO$_3$/water solution. The reaction mixture was evaporated to dryness under a flow of nitrogen overnight. Then 55 mL of anhydrous methanol along with 5 drops of concentrated H$_2$SO$_4$ were added to the reactor. The mixture was stirred at 95° C. for 6 hours. After cooling to room temperature, a solid precipitated and was filtered. The crude product (3.26 g) (LC purity=93%) was obtained as the first portion of product. The filtrate was concentrated on a rotary evaporator to remove most of the solvent. The wet solid paste was then extracted with ethyl acetate. The ethyl acetate mixture was washed with water and dried over MgSO$_4$. The solvent was removed with a rotary evaporator. Additional crude product (2.56 g) (LC purity=81%) was obtained in this second portion. Both portions of crude product were combined and re-crystallized from methanol giving 4.3 g (57% yield, LC purity=97%) of product. The methanol mother liquid was put in the refrigerator over the weekend. An additional 0.14 g (96% LC purity) of product was obtained: mp 194-196° C. $^1$H NMR (THF-d$_8$, 300 MHz) δ 7.29 (d, 1H, J=6 Hz), 6.06 (s, 2H), 3.71 (s, 3H); $^{13}$C NMR (THF-d$_8$, 75 MHz, $^1$H decoupled) δ 164.0 (s), 147.2 (s), 144.0 (m), 127.9 (d, J=20 Hz), 112.8 (d, J=5 Hz), 51.5 (s). EIMS m/z=250, 248 (M$^+$, 1 Br, 9%), 220 (14%), 218 (15%), 192 (95%), 191 (31%), 190 (100%), 189 (27%), 164 (10%), 162 (10%), 137 (7%), 111 (12%), 110 (19%), 109 (10%), 84 (9%), 83 (14%), 82 (10%).

Example 8

Methyl 4-(acetylamino)-3,6-dichloro-5-fluoro-picolinate

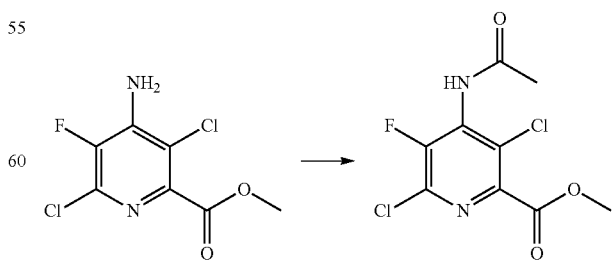

In a 50 mL three-neck round-bottomed flask was charged the methyl 4-amino-3,6-dichloro-5-fluoropicolinate (12.1 mmol), toluene (50 mL), and CHCl$_3$ (15 mL). To this suspension was added dropwise a premixed solution of sulfuric acid (0.05 mmol) and acetic anhydride (24.2 mmol), in toluene (5 mL). The reaction mixture was then heated, under a N$_2$ stream, to 55-60° C. and the reaction was monitored by TLC. Once the reaction was deemed complete the heating mantle was removed and the reaction solution was cooled to ambient temperature. The mixture was then added dropwise to a mixture of saturated aqueous NaHCO$_3$/toluene/CHCl$_3$ (180 mL, 3/10/5), stirred for 20 min, and the layers separated using a reparatory funnel. To the organic layer was added silica gel (14.8 g) and the solvent was removed using a rotary evaporator. The crude product on silica was then purified using a Combi-Flash silica gel purification system using ethyl acetate and hexane as eluents. The purity of the product was analyzed by HPLC: mp=183-186° C.; $^1$H NMR (400 MHz, DMSO-d$_6$) δ 10.5 (s, 1H, NH), 3.93 (s, 3H), 2.17 (s, 3H); $^{13}$C NMR (100.6 MHz, DMSO-d$_6$) δ 167.9, 162.8, 151.7, 149.0, 142.8 (d, J$_{F-C}$=24 Hz), 136.2 (d, J$_{F-C}$=80 Hz), 134.7 (d, J$_{F-C}$=56 Hz), 126.6, 53.2, 22.5; $^{19}$F NMR (376.5 MHz, DMSO-d$_6$) δ −114.5; MS Calcd. for C$_9$H$_7$Cl$_2$FN$_2$O$_3$: 280.0. Found: 281 (MH$^+$), 245, 180.

Example 9

Methyl 4-(acetylamino)-6-bromo-3-chloro-5-fluoro-picolinate

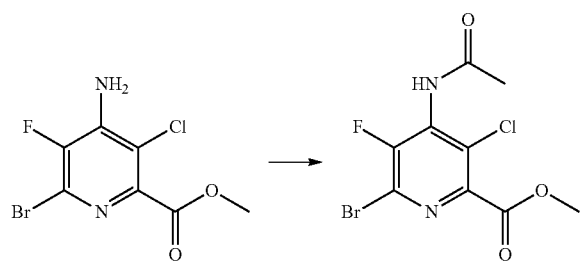 [SMILES: COC(=O)c1nc(Cl)c(F)c(N)c1Cl ; COC(=O)c1nc(Cl)c(F)c(NC(C)=O)c1Cl]

Methyl 4-(acetylamino)-6-bromo-3-chloro-5-fluoro-picolinate was prepared in analogous fashion to methyl 4-(acetylamino)-3,6-dichloro-5-fluoro-picolinate in Example 8 except that methyl 4-amino-6-bromo-3-chloro-5-fluoropicolinate was used in place of methyl 4-amino-3,6-dichloro-5-fluoropicolinate: mp=190-192° C.; $^1$H NMR (400 MHz, DMSO-d$_6$) δ 10.5 (s, 1H), 3.93 (s, 3H), 2.16 (s, 3H); $^{13}$C NMR (100.6 MHz, DMSO-d$_6$) δ 168.0, 162.8, 153.1, 150.5, 143.7 (d, J$_{F-C}$=24 Hz), 134.1 (d, J$_{F-C}$=56 Hz), 127.3 (d, J$_{F-C}$=96 Hz), 53.2, 22.5; $^{19}$F NMR (376.5 MHz, DMSO-d$_6$) δ −108.3; MS Calcd. for C$_9$H$_7$BrCl$_2$FN$_2$O$_3$: 323.93. Found: 289, 226.

Example 10

Isopropyl 4-(amino)-6-(4-chloro-2-fluoro-3-methoxyphenyl)-5-fluoro-picolinate

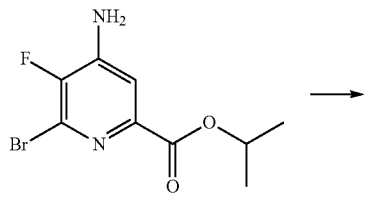

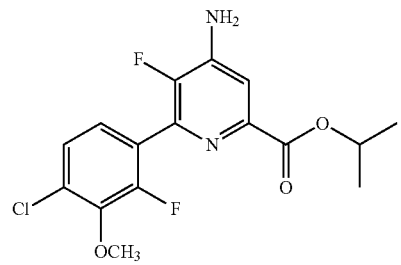

In a 50 mL three-neck round bottom flask was charged potassium fluoride dihydrate (12.0 mmol), 2-(4-chloro-2-fluoro-3-methoxyphenyl)-1,3,2-dioxaborinane (5.40 mmol), isopropyl 4-amino-6-bromo-5-fluoropicolinate (4.0 mmol), MeCN (15 mL), and H$_2$O (5 mL). The resulting mixture was sparged with N$_2$ for 15 min then Pd(PPh$_3$)$_2$Cl$_2$ (0.006-0.08 mmol) was added. The resulting suspension was sparged for 20 min then heated to 68-70° C. After 1 h of stirring, an aliquot (1-2 μL) was taken and diluted with MeCN (2 mL). The aliquot was analyzed by HPLC by monitoring the consumption of starting material 4-(acetylamido)-5-fluoropicolinate ester. After the reaction was deemed complete the heating mantle was removed and the mixture was cooled to ambient temperature and was diluted with MeCN/toluene/H$_2$O (75 mL, 3/1/1); if needed, extra volume of the solvent mixture was added to dissolve the solids. The layers were then separated using a reparatory funnel. The product assay was then determined using an internal standard (hexanophenone): mp=177-179° C.; $^1$H NMR (400 MHz, DMSO-d$_6$) δ 7.52 (d, J$_{F-H}$=6.8 Hz, 1H), 7.47 (dd, J=8.4, 1.6 Hz, 1H), 7.29 (dd, J=8.4, 7.2 Hz, 1H), 6.70 (s, 2H), 5.12 (p, J=6.4 Hz, 1H), 3.93 (s, 3H), 1.30 (d, J=6.4 Hz, 6H); $^{13}$C NMR (100.6 MHz, DMSO-d$_6$) δ 163.6, 154.4, 151.2, 148.0, 145.5, 144.0 (dd, J$_{F-C}$=38.3, 4.2 Hz), 143.7 (d, J$_{F-C}$=2.9 Hz), 139.0 (d, J$_{F-C}$=13.6 Hz), 128.2 (d, J$_{F-C}$=3.1 Hz), 126.0 (d, J$_{F-C}$=3.4 Hz), 125.4 (d, J$_{F-C}$=3.5 Hz), 123.9 (dd, J$_{F-C}$=14.2, 3.5 Hz), 112.5 (d, J$_{F-C}$=5.1 Hz), 68.5, 61.5 (d, J$_{F-C}$=4.0 Hz), 21.6; $^{19}$F{$^1$H} NMR (376.5 MHz, DMSO-d$_6$) δ −129.4 (d, J$_{F-F}$=25.6 Hz), −142.8 (d, J$_{F-F}$=25.6 Hz); MS Calcd. for C$_{16}$H$_{15}$ClF$_2$N$_2$O$_3$: 356.1. Found: 356 (M$^+$), 270.

Example 11

Methyl 4-(amino)-3-chloro-6-(4-chloro-2-fluoro-3-methoxyphenyl)-5-fluoro-picolinate

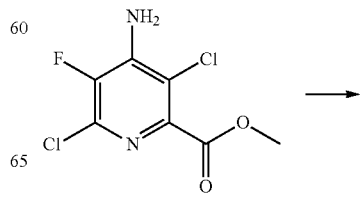

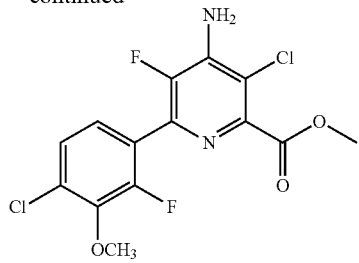

Methyl 4-(amino)-3-chloro-6-(4-chloro-2-fluoro-3-methoxyphenyl)-5-fluoro-picolinate was prepared in analogous fashion to isopropyl 4-(amino)-6-(4-chloro-2-fluoro-3-methoxyphenyl)-5-fluoro-picolinate in Example 10 except that methyl 4-amino-3,6-dichloro-5-fluoropicolinate was used in place of isopropyl 4-amino-6-bromo-5-fluoropicolinate: mp=169-171° C.; $^1$H NMR (400 MHz, DMSO-d$_6$) δ 7.46 (dd, J=8.8, 1.6 Hz, 1H), 7.29 (dd, J=8.8, 7.2 Hz, 1H), 7.10 (s, 2H), 3.93 (s, 3H), 3.87 (s, 3H); $^{13}$C NMR (100.6 MHz, DMSO-d$_6$) δ 164.8, 154.3, 151.8, 146.2, 144.5, 143.9-143.7 (m), 141.6 (d, J$_{F-C}$=14.0 Hz), 136.3 (d, J$_{F-C}$=13.4 Hz), 128.5 (d, J$_{F-C}$=2.6 Hz), 125.5 (d, J$_{F-C}$=3.6 Hz), 122.9 (d, J$_{F-C}$=13.7, 4.0 Hz), 61.6 (d, J$_{F-C}$=4.2 Hz), 52.7; $^{19}$F {$^1$H} NMR (376.5 MHz, DMSO-d$_6$) δ -129.2 (d, J$_{F-F}$=27.5 Hz), -137.7 (d, J$_{F-F}$=27.1 Hz); IR: 3482, 3381, 2950, 1741, 1612, 1466, 1423, 1366, 1228, 1202, 1045, 970, 905, 815; MS Calcd. for C$_{14}$H$_{11}$Cl$_2$F$_2$N$_2$O$_3$: 362.0. Found: 362 (M$^+$), 304.

Example 12

Methyl 4-(acetylamino)-3-chloro-6-(4-chloro-2-fluoro-3-methoxyphenyl)-5-fluoro-picolinate

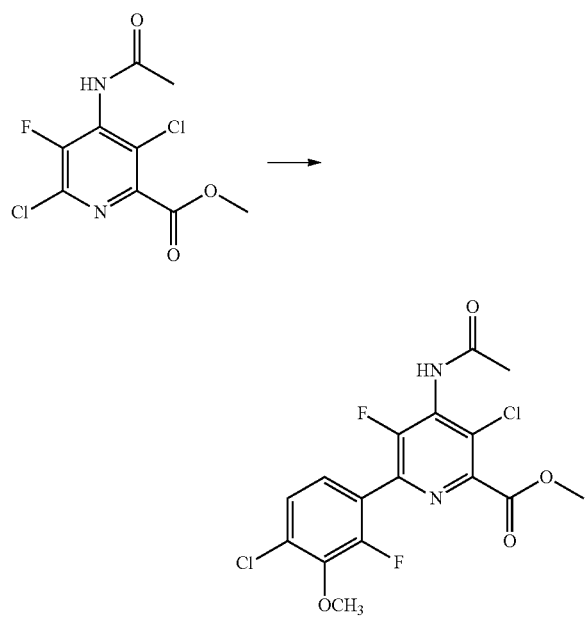 [SMILES: COC(=O)c1nc(Cl)c(F)c(NC(C)=O)c1Cl ; COC(=O)c1nc(-c2ccc(Cl)c(OC)c2F)c(F)c(NC(C)=O)c1Cl]

Methyl 4-(acetylamino)-3-chloro-6-(4-chloro-2-fluoro-3-methoxyphenyl)-5-fluoro-picolinate was prepared in analogous fashion to isopropyl 4-(amino)-6-(4-chloro-2-fluoro-3-methoxyphenyl)-5-fluoro-picolinate in Example 10 except that methyl 4-acetamido-3,6-dichloro-5-fluoropicolinate was used in place of isopropyl 4-amino-6-bromo-5-fluoropicolinate: mp=175-177° C.; $^1$H NMR (400 MHz, DMSO-d$_6$) δ 7.52 (dd, J=8.4, 1.6 Hz, 1H), 7.38 (dd, J=8.4, 7 Hz, 1H), 3.95 (d, J=0.8 Hz, 3H), 3.94 (s, 3H), 2.17 (s, 3H); $^{13}$C NMR (100.6 MHz, DMSO-d$_6$) δ 168.0, 163.9, 154.4, 153.7, 151.9, 151.0, 144.9 (d, J$_{F-C}$=4.4 Hz), 143.9 (d, J$_{F-C}$=13.3 Hz), 139.5 (d, J$_{F-C}$=16.7 Hz), 133.7 (d, J$_{F-C}$=14.4 Hz), 129.3 (d, J$_{F-C}$=3.2 Hz), 126.7, 125.9 (dd, J$_{F-C}$=14.6, 3.6 Hz), 121.9 (d, J$_{F-C}$=13.2, 4.3 Hz), 61.7 (d, J$_{F-C}$=4.4 Hz), 53.1, 22.5; $^{19}$F{$^1$H} NMR (376.5 MHz, DMSO-d$_6$) δ -119.0 (d, J$_{F-F}$=28.6 Hz), -129.0 (d, J$_{F-F}$=28.6 Hz); IR: 3182, 3008, 2952, 1736, 1674, 1512, 1464, 1422, 1401, 1372, 1263, 1238, 1213, 1173, 1049, 1026, 977, 904, 687; MS Calcd. for C$_{16}$H$_{12}$Cl$_2$F$_2$N$_2$O$_4$: 404.0. Found: 404 (M$^+$), 369.

Example 13

Methyl 4-(acetylamino)-6-(4-chloro-2-fluoro-3-methoxyphenyl)-5-fluoro-picolinate

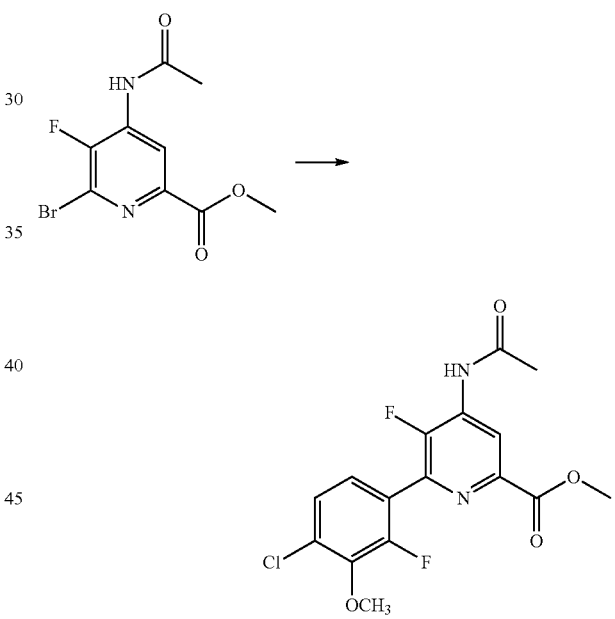

Methyl 4-(acetylamino)-6-(4-chloro-2-fluoro-3-methoxyphenyl)-5-fluoro-picolinate was prepared in analogous fashion to isopropyl 4-(amino)-6-(4-chloro-2-fluoro-3-methoxyphenyl)-5-fluoro-picolinate in Example 10 except that methyl 4-acetamido-6-bromo-5-fluoropicolinate was used in place of isopropyl 4-amino-6-bromo-5-fluoropicolinate: mp=189-191° C.; $^1$H NMR (400 MHz, DMSO-d$_6$) δ 10.5 (s, 1H), 9.04 (d, J$_{F-H}$=5.6 Hz, 1H), 7.53 (dd, J=8.4, 1.6 Hz, 1H), 7.37 (dd, J=8.4, 7.0 Hz, 1H), 3.95 (s, 3H), 3.89 (s, 3H), 2.22 (s, 3H); $^{13}$C NMR (100.6 MHz, DMSO-d$_6$) δ 170.3, 164.1, 154.4, 151.9, 149.4, 146.7, 144.1-143.8 (m), 140.5 (d, J$_{F-C}$=15.3 Hz), 135.1 (d, J$_{F-C}$=10.8 Hz), 128.9 (d, J$_{F-C}$=3.4 Hz), 125.9 (dd, J$_{F-C}$=35.0, 3.5 Hz), 122.9 (dd, J$_{F-C}$=13.7, 3.5 Hz), 61.6, 52.6, 24.1; $^{19}$F {$^1$H} NMR (376.5 MHz, DMSO-d$_6$) δ -129.5 (d, J$_{F-F}$=27.5 Hz), -142.8 (d, J$_{F-F}$=27.5 Hz); IR: 3341, 2972, 2944, 1733, 1705, 1599, 1507, 1439, 1416, 1406, 1371, 1283, 1166, 1039, 974, 926, 890, 823, 678; MS Calcd. for $C_{16}H_{13}ClF_2N_2O_4$: 370.1. Found: 370 (M+), 312.

Example 14

4,5-Dichloro-6-(4-chloro-2-fluoro-3-methoxyphenyl)picolinic acid

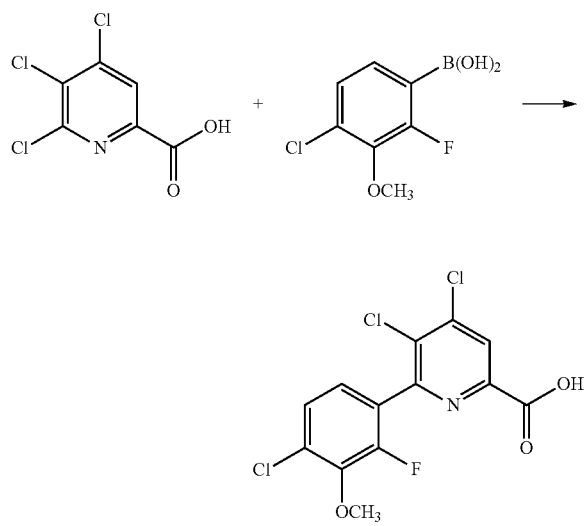

To a 50 mL three-necked flask equipped with a stirring bar and a condenser were placed 4,5,6-trichloropicolinic acid (0.503 g, 90% purity, 2 mmol), triethylamine (0.607, 6 mmol), acetonitrile (5 g) and water (5 g). The mixture became a homogeneous solution which was sparged with nitrogen for 15 minutes. Bis(triphenylphosphine)palladium(II) dichloride (0.042 g, 0.06 mmol) was added and the mixture was heated to 50° C. In a one-necked flask were placed (4-chloro-2-fluoro-3-methoxyphenyl)-boronic acid (1.951 g, 22 wt % in methyl isobutyl ketone/dimethoxyethane, 2.1 mmol) and acetonitrile (2.5 g). The solution was sparged with nitrogen for 15 minutes, and then slowly added to trichloropicolinic acid solution by a syringe pump at 50° C. The total addition time was about two hours. The reaction mixture was stirred at 50° C. for three more hours. A sample was taken and analyzed by HPLC. The LC results indicated that the reaction was completed. The reaction mixture was allowed to cool to room temperature. To acidify the reaction mixture, hydrochloric acid (6 g, 1 N HCl in water) was added to the flask dropwise. The resulting slurry was stirred overnight. The mixture was filtered and a light brown solid was obtained. This crude product was stirred in acetonitrile at room temperature for 2 hours. After filtration and vacuum drying, the white product (0.44 g, 92% LC purity, 58% yield) was obtained. $^1$H NMR (400 MHz, THF-$d_8$) δ 8.35 (s, 1H), 7.40 (dd, J=8.5, 1.7 Hz, 1H), 7.23 (dd, J=8.5, 6.9 Hz, 1H), 4.00 (d, J=1.3 Hz, 3H); $^{13}$C NMR (101 MHz, THF-$d_8$) δ 163.62 (s), 154.81 (s), 153.03 (s), 152.31 (s), 147.36 (s), 144.64 (d, J=13.4 Hz), 143.70 (s), 133.21 (s), 129.55 (d, J=3.5 Hz), 126.34 (d, J=14.4 Hz), 125.71 (s), 125.41-125.01 (m), 60.91 (d, J=4.8 Hz); $^{19}$F NMR (376 MHz, THF-$d_8$) δ +−128.96. ESI/LC/MS/PI (M+ H)+=349.9559 (100%), 351.9531 (99.66%), 353.95 (33.59%).

Example 15

6-(4-Chloro-2-fluoro-3-methoxyphenyl)-4,5-dichloro-2-pyridinecarbonyl chloride

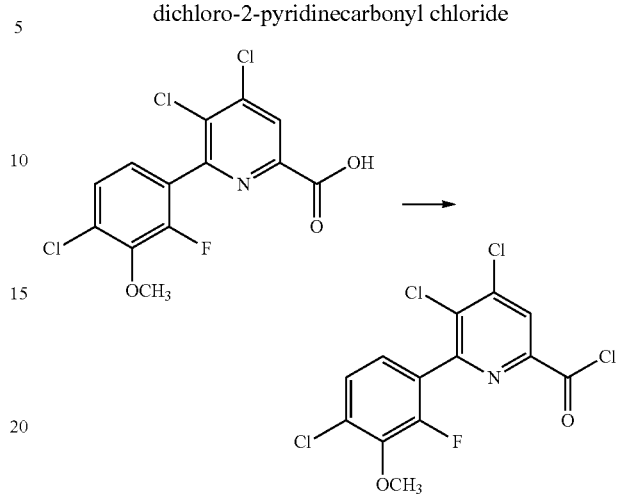

A mixture of 33.5 g (~95 mmol) of 6-(4-chloro-2-fluoro-3-methoxyphenyl)-4,5-dichloro-2-pyridinecarboxylic acid, 10.2 mL (140 mmol) of thionyl chloride, 0.1 mL of N,N-dimethylforamide (DMF) and 200 mL of toluene was heated at 75° C. for 5 h. The reaction progress was monitored by conversion of the acid chloride to its methyl ester (one drop of reaction mixture added to 5 drops of a 10% wt methanol solution containing 4-(dimethylamino)pyridine, briefly heating to reflux, dilution with acetonitrile and injection). LC analysis indicated 8 area % remaining carboxylic acid and 3 area % of an unidentified closely following product. Another 5 mL of thionyl chloride and 0.1 mL of DMF were added, and heating continued for an additional 2 h. LC analysis indicated methyl ester product, carboxylic acid gone with only the unidentified polar peak remaining After stirring at RT overnight, the reaction mixture was filtered to remove a small amount of an insoluble material. The filtrate was concentrated in vacuo, and toluene added twice and re-concentrated in vacuo to evaporate residual thionyl chloride. The white solid (38.6 g) was dried in a vacuum oven at 40° C. to give 33.3 g of title compound (mp 134-136° C.). LC internal standard analysis (conversion to its methyl ester as described above) indicated 98.1 wt %. EIMS m/e (relative intensity) 369 (4Cl, 80), 332 (3Cl, 38), 304 (3Cl, 82), 269 (2Cl, 100), 254 (2Cl, 30), 226 (2Cl, 73), 191 (30), 156 (46); $^1$H NMR (400 MHz, CDCl$_3$) δ 8.23 (s, 1H), 7.32 (dd, J=8, 2 Hz, 1H), 7.15 (dd, J=8, 7 Hz, 1H), 4.02 (dd, J=1 Hz, 3H); $^{19}$F NMR (376 MHz, $^1$H decoupled, CDCl$_3$) δ −126.83.

Example 16

Methyl 6-(4-chloro-2-fluoro-3-methoxyphenyl)-4,5-difluoro-2-pyridinecarboxylate

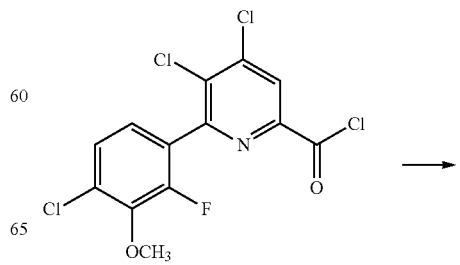

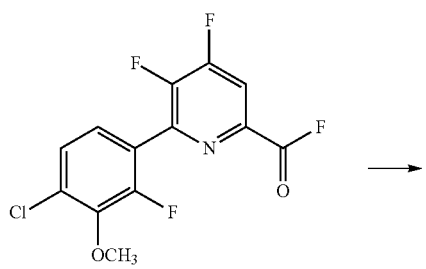

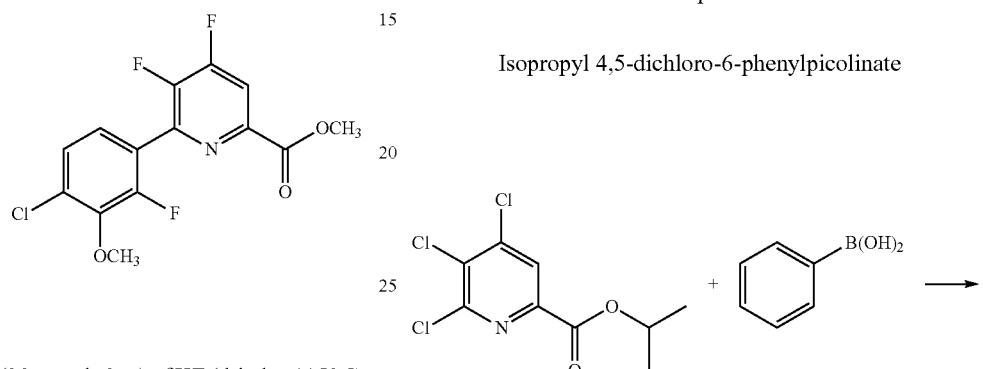

A mixture of 1.74 g (30 mmol, 6 eq) of KF (dried at 115° C. with $N_2$ purge overnight), 1.85 g (5 mmol) of 6-(4-chloro-2-fluoro-3-methoxyphenyl)-4,5-dichloro-2-pyridinecarbonyl chloride and 10 mL of sulfolane (dried 4 A molecular sieves) was heated at 130° C. for 10 h and then at RT overnight. LC area analysis indicated incomplete reaction (63% product, 15% mono-fluoro intermediates). The mixture was heated at 130° C. for another 7 h, when LC area analysis indicated 74% product and 4% mono-fluoro intermediates. Data for the intermediate acid fluoride: EIMS m/e (relative intensity) 319 (1Cl, 100), 304 (1Cl, 20), 276 (1Cl, 56), 241 (11), 228 (8), 213 (12), 194 (18), 174 (5). $^{19}$F NMR (376 MHz, sulfolane) δ 17.84 (s), −123.40−−123.54 (m), −129.29 (dd, J=29, 7 Hz), −137.70 (ddd, J=29, 21, 5 Hz). $^{19}$F NMR (376 MHz, $^1$H decoupled, sulfolane) δ 17.84 (br s), −123.38−−123.58 (m), −129.29 (d, J=29 Hz), −137.70 (dd, J=29, 21 Hz).

After cooling to 50° C., 0.24 mL (6 mmol) of MeOH was added, and the mixture stirred at RT overnight. To the amber mixture was added 10 mL of $H_2O$ dropwise over 20 min. Initially, gummy solids formed which eventually dissipated to leave a thick, brownish gray mixture. After stirring at RT for 15 min, the mixture was filtered, rinsed with 4 mL of 1:1 sulfolane/$H_2O$ and 2× with 4 mL of $H_2O$ to give 5.44 g of a brown solid. The solid was air dried to give 1.54 g of a tan powder. LC internal standard analysis indicated a purity of 78.4 wt %, for a yield of 73.0%.

Material from the fluorination experiment above (1.8 g, 67 area % LC) was heated and dissolved in 15 mL of toluene. This solution was flash chromatographed on silica (500 g, 70-230 mesh) eluting with toluene. After 10 L of toluene has passed through the column, product was seen and collected over the next 2 L of eluent. The toluene fractions containing the product were concentrated in vacuo to give 647 mg of a white solid, 94 area % purity by LC analysis. This solid was dissolved in 3 mL of acetonitrile, cooled in a refrigerator, filtered and rinsed with 0.5 mL of cold acetonitrile to give 529 mg of a white solid after drying in a hood overnight, mp 134-134° C., 97 area % purity by LC analysis. EIMS m/e (relative intensity) 331 (1Cl, 50), 273 (1Cl, 100), 238 (46), 237 (28), 222 (14), 194 (48); $^1$H NMR (400 MHz, DMSO) δ 8.05 (dd, J=9, 6 Hz, 1H), 7.35-7.27 (m, 2H), 4.01 (s, 3H), 4.00 (d, J=1 Hz, 3H); $^{19}$F NMR (376 MHz, $^1$H decoupled, CDCl$_3$) δ −123.64 (d, J=20 Hz), −128.51 (d, J=31 Hz), −139.59 (dd, J=31, 20 Hz); $^{19}$F NMR (376 MHz, CDCl$_3$) δ −123.64 (dd, J=19, 9 Hz), −128.51 (dd, J=31, 6 Hz), −139.59 (ddd, J=31, 19, 6 Hz).

Example 17

Isopropyl 4,5-dichloro-6-phenylpicolinate

In a 125 mL three-neck round bottom flask was charged potassium fluoride dihydrate (4.52 g, 38.0 mmol), phenylboronic acid (4.88 g, 40 mmol), isopropyl 4,5,6-trichloropicolinate ester (4.28 g, 16.0 mmol), MeCN (60 mL), and $H_2O$ (20 mL). The resulting suspension was sparged with $N_2$ for 15 min then bis(triphenylphosphine)palladium (II) chloride (0.45 g, 0.64 mmol) was added. The resulting yellow suspension was then sparged for 15 min then heated to 65-68° C. After 1 h of stirring an aliquot (1-2 μL) was taken and diluted with MeCN (2 mL). The aliquot was analyzed by HPLC by monitoring the consumption of starting material isopropyl 4,5,6-trichloropicolinate ester. After 3 h the reaction was deemed complete. The heating mantle was removed and the mixture cooled to ambient temperature and diluted with MeCN/EtOAc/$H_2O$ (150 mL, 2/2/1). The layers were then separated using a separating funnel and to the organic layer was added silica gel (22 g). The solvent was removed in vacuo and the solid purified by CombiFlash using a 220 g column. Concentration of the aliquots gave a white solid weighing 4.07 g (82%). mp=94-96° C.; $^1$H NMR (400 MHz, CDCl$_3$) δ 8.12 (s, 1H), 7.74-7.71 (m, 2H), 7.49-7.46 (m, 3H), 5.31 (h, J=6.4 Hz, 1H), 1.41 (d, J=6.4 Hz, 6H); $^{13}$C NMR (100.6 MHz, CDCl$_3$) δ 163.1, 158.6, 146.5, 144.3, 137.5, 132.1, 129.6, 129.4, 128.0, 125.0, 70.2, 21.8; MS Calcd. For C$_{15}$H$_{13}$Cl$_2$N$_2$O$_2$: 309.03. Found: 309 (M$^+$), 223, 188, 152, 125.

Example 18

Isopropyl 4,5-dichloro-6-(4-methoxyphenyl)picolinate

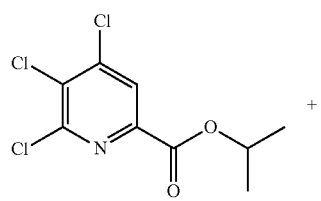

+

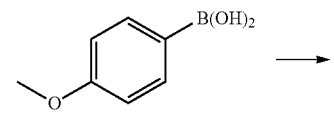

→

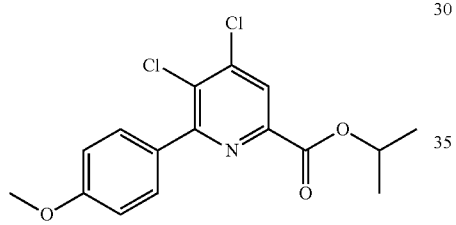

70.1, 55.3, 21.8; MS Calcd. For C$_{16}$H$_{15}$Cl$_2$NO$_3$: 339.04. Found: 339 (M$^+$), 253, 218, 203, 182.

Example 19

Isopropyl 4,5-dichloro-6-(4-chlorophenyl)picolinate

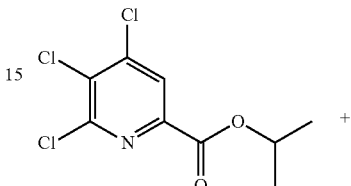

+

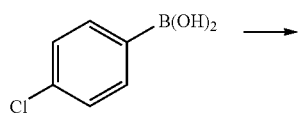

→

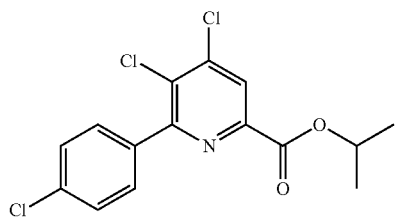

In a 125 mL three-neck round bottom flask was charged potassium fluoride dihydrate (5.65 g, 60.0 mmol), 4-methoxyphenylboronic ester (3.42 g, 22.5 mmol), isopropyl 4,5,6-trichloropicolinate ester (4.00 g, 15.0 mmol), MeCN (72 mL), and H$_2$O (24 mL). The resulting suspension was sparged with N$_2$ for 15 min then bis(triphenylphosphine)palladium (II) chloride (0.42 g, 0.60 mmol) was added. The resulting yellow suspension was then sparged for 15 min then heated to 60-62° C. After 1 h of stirring an aliquot (1-2 µL) was taken and diluted with MeCN (2 mL). The aliquot was analyzed by HPLC by monitoring the consumption of starting material isopropyl 4,5,6-trichloropicolinate ester. After 3 h the reaction was deemed complete. The heating mantle was removed and the mixture cooled to ambient temperature and diluted with MeCN/PhMe/H$_2$O (100 mL, 4/3/3). The layers were separated using a separating funnel and to the organic layer was added silica gel (22 g). The solvent was removed in vacuo and solid purified by CombiFlash to give a white solid weighing 2.90 g (57%). mp=113-116° C.; $^1$H NMR (400 MHz, CDCl$_3$) δ 8.07 (s, 1H), 7.74 (dt, J=9.2, 2.8 Hz, 2H), 6.99 (dt, J=8.8, 2.8 Hz, 2H), 5.30 (h, J=6.0 Hz, 1H), 3.87 (s, 3H), 1.41 (d, J=6.0 Hz, 6H); $^{13}$C NMR (100.6 MHz, CDCl$_3$) δ 163.2, 160.6, 158.1, 146.4, 144.2, 131.7, 131.2, 129.9, 124.4, 113.4, In a 125 mL three-neck round bottom flask was charged potassium fluoride dihydrate (4.52 g, 38.0 mmol), 4-chlorophenylboronic ester (5.00 g, 32.0 mmol), isopropyl 4,5,6-trichloropicolinate ester (4.28 g, 16.0 mmol), MeCN (70 mL), and H$_2$O (23 mL). The resulting suspension was sparged with N$_2$ for 15 min then bis(triphenylphosphine)palladium(II) chloride (0.45 g, 0.64 mmol) was added. The resulting yellow suspension was then sparged for 15 min then heated to 65-68° C. After 1 h of stirring an aliquot (1-2 µL) was taken and diluted with MeCN (2 mL). The aliquot was analyzed by HPLC by monitoring the consumption of starting material isopropyl 4,5,6-trichloropicolinate ester. After 3 h the reaction was deemed complete. The heating mantle was removed and the mixture cooled to ambient temperature and diluted with MeCN/PhMe/H$_2$O (80 mL, 2/3/2). The layers were then separated using a separating funnel and to the organic layer was added silica gel (22.5 g). The solvent was removed in vacuo and the solid was purified by CombiFlash to afford after solvent concentration white solid weighing 3.44 g (62%). mp=133-135° C.; $^1$H NMR (400 MHz, CDCl$_3$) δ 8.13 (s, 1H), 7.69 (dt, J=8.8, 2.0 Hz, 2H), 7.29 (dd, J=8.4, 2.0 Hz, 2H), 5.31 (h, J=6.0 Hz, 1H), 1.41 (d, J=6.0 Hz, 6H); $^{13}$C NMR (100.6 MHz, CDCl$_3$) δ 162.9, 157.4, 146.6, 144.5, 135.8, 135.7, 132.0, 131.0, 128.3, 125.2, 70.3, 21.8; MS Calcd. For C$_{15}$H$_{12}$Cl$_3$NO$_2$: 342.99. Found: 343 (M$^+$), 257, 222, 186, 151.

Example 20

4,5-Dichloro-6-(4-methoxyphenyl)picolinic acid

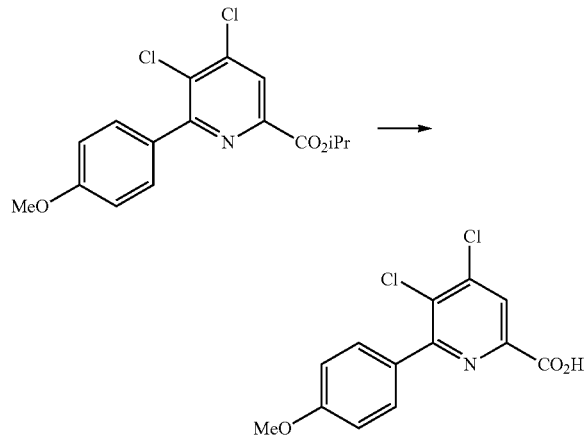

To a mixture of isopropyl 4,5-dichloro-6-(4-methoxyphenyl)picolinate (5.25 g, 15.4 mmol) in tetrahydrofuran (40 mL) and water (10 mL) was added potassium hydroxide (1.26 g, 22.4 mmol). The reaction mixture was allowed to stir at room temperature for 12 h. After 1 hour of stirring, solids precipitated from the mixture. HCl (aq) (2N, 25 mL) was added to the reaction mixture, and it formed a clear biphasic mixture. The mixture was added to water (75 mL) in a reparatory funnel and extracted with EtOAc (2×75 mL). The combined organic layers were washed with water (25 mL) and saturated NaCl (50 mL) and then concentrated under reduced pressure to provide 4.57 g (99% yield) of 4,5-dichloro-6-(4-methoxyphenyl)picolinic acid as a white solid. $^1$H NMR (400 MHz, CDCl$_3$) δ 8.23 (s, 1H), 7.72-7.64 (m, 2H), 7.07-6.99 (m, 2H), 3.89 (s, 3H); $^{13}$C NMR (101 MHz, CDCl$_3$) δ 162.78, 161.05, 157.26, 146.30, 143.76, 133.54, 130.98, 128.72, 123.45, 113.77, 55.48; mp=164-181° C.

Example 21

4,5-Dichloro-6-(4-chlorophenyl)picolinic acid

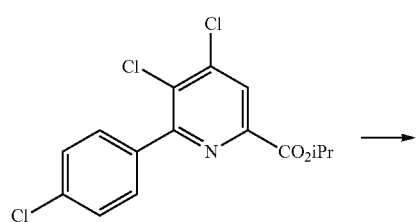

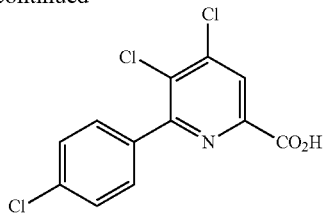

To a 125 mL 3-neck round bottom flask fitted with a condenser, nitrogen inlet, overhead stirrer, thermometer and heating mantle was charged isopropyl 4,5-dichloro-6-(4-chlorophenyl)picolinate (7.6 g, 22.1 mmol) and isopropyl alcohol (70 mL). Reaction mixture was heated to 40° C. and potassium hydroxide (85%, 5.1 g, 77.4 mmol) and water (5 mL) were added. Solids precipitated from the mixture, and it became difficult to stir. The mixture was diluted with water (250 mL) to dissolve most of the solids and allowed to stir at room temperature. Concentrated HCl (12 N, 5.6 mL) was added dropwise to the reaction mixture to achieve a pH of ~2 and solids precipitated from the mixture. The solids were isolated by vacuum filtration and washed with water (2×100 mL), then allowed to dry to give 7.3 g (108% yield by weight) of 4,5-dichloro-6-(4-chlorophenyl)picolinic acid as a white solid. $^1$H NMR (400 MHz, THF-d$_8$/D$_2$O) δ 8.19 (d, J=11.2 Hz, 1H), 7.84-7.73 (m, 2H), 7.50 (dd, J=10.3, 3.5 Hz, 2H); $^{13}$C NMR (101 MHz, THF-d$_8$/D$_2$O) δ 167.70, 156.03, 152.40, 143.60, 136.49, 134.76, 131.22, 129.24, 128.04, 124.71; mp=229° C.

Example 22

4,5-Dichloro-6-(phenyl)picolinic acid

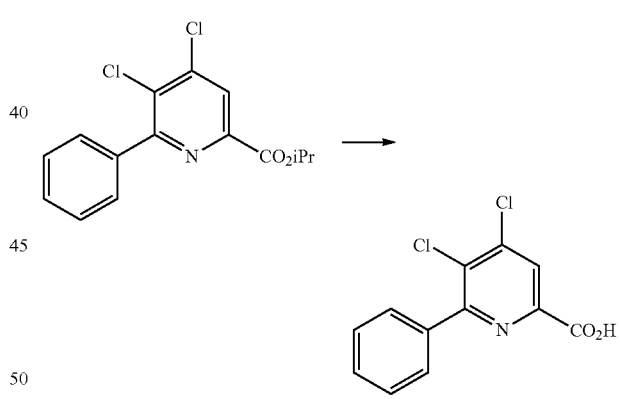

To a 125 mL 3-neck round bottom flask fitted with a condenser, nitrogen inlet, overhead stirrer, thermometer and heating mantle was charged isopropyl 4,5-dichloro-6-phenyl picolinate (7.0 g, 22.5 mmol) and isopropyl alcohol (65 mL). Reaction mixture was heated to 40° C. and potassium hydroxide (85%, 5.1 g, 77.4 mmol) and water (5 mL) were added. Solids precipitated from the mixture and it became difficult to stir. The mixture was diluted with water (250 mL) to dissolve most of the solids and allowed to stir at rt. Concentrated sulfuric acid (5 mL) was added dropwise to the reaction mixture to achieve a pH of ~2 and solids precipitated from the mixture. The solids were isolated by vacuum filtration and washed with water (2×100 mL), then allowed to dry to give 5.8 g (96% yield) of 4,5-dichloro-6-phenylpicolinic acid as a white solid. $^1$H NMR (400 MHz, CDCl$_3$) δ 8.28 (s, 1H), 7.74-7.60 (m, 2H), 7.59-7.45 (m, 3H), 5.98 (br s, 1H); $^{13}$C NMR (101 MHz, CDCl₃) δ 162.97, 157.76, 146.26, 144.00, 136.51, 133.84, 130.02, 129.26, 128.38, 124.16; mp=. 159-160° C.

Example 23

4,5-Dichloro-6-(4-chlorophenyl)picolinoyl chloride

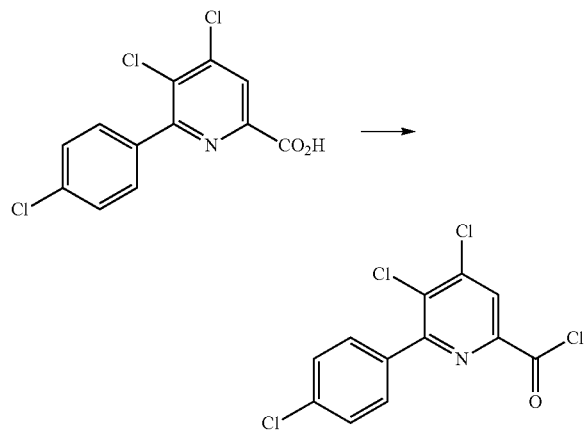

To a mixture of 4,5-dichloro-6-(4-chlorophenyl)picolinic acid (3.00 g, 9.9 mmol) in toluene (25 mL) was added thionyl chloride (1.08 mL, 14.9 mmol) and dimethylformamide (0.04 mL, 0.5 mmol). Reaction mixture was heated at 80° C. for 2.5 h. HPLC analysis of an aliquot of the reaction mixture treated with methanol and dimethylaminopyridine indicated starting material remaining Reaction mixture was allowed to cool to rt and additional thionyl chloride (0.5 mL, 6.9 mmol) and dimethylformamide (0.04 mL, 0.5 mmol) were added. Reaction was heated at 80° C. for 2 h. Reaction was allowed to cool to room temperature and concentrated under reduced pressure to provide a white solid. Toluene (40 mL) was added to dissolve the solid and concentrated under reduced pressure and then this process was performed a second time. 4,5-Dichloro-6-(4-chlorophenyl)picolinoyl chloride was isolated as a white solid (3.05 g, 96% yield). ¹H NMR (400 MHz, CDCl₃) δ 8.15 (s, 1H), 7.79-7.72 (m, 2H), 7.53-7.46 (m, 2H); ¹³C NMR (101 MHz, CDCl₃) δ 168.66, 157.63, 146.48, 145.44, 136.35, 135.10, 134.28, 131.04, 128.63, 124.90. MS Calcd. for $C_{12}H_5Cl_4NO$: 320.91. Found: 257, 222, 207, 186, 151.

Example 24

4,5-Dichloro-6-(phenyl)picolinoyl chloride

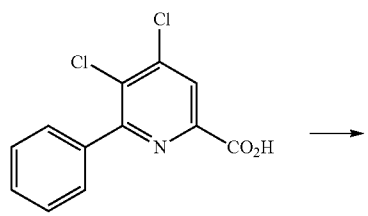

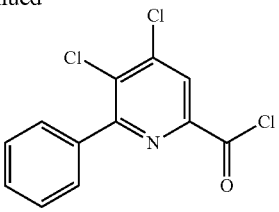

To a mixture of 4,5-dichloro-6-phenylpicolinic acid (3.00 g, 11.2 mmol) in toluene (40 mL) was added thionyl chloride (1.22 mL, 16.8 mmol) and dimethylformamide (0.04 mL, 0.6 mmol). Reaction mixture was heated at 80° C. for 3 h. HPLC analysis of an aliquot of the reaction mixture treated with methanol and dimethylaminopyridine indicated complete conversion of the starting material. Reaction was allowed to cool to room temperature and concentrated under reduced pressure to provide a white solid. Toluene (40 mL) was added to dissolve the solid and concentrated under reduced pressure and then this process was performed a second time. 4,5-Dichloro-6-phenylpicolinoyl chloride was isolated as a white solid (2.84 g, 89% yield). ¹H NMR (400 MHz, CDCl₃) δ 8.14 (s, 1H), 7.83-7.75 (m, 2H), 7.55-7.47 (m, 3H); ¹³C NMR (101 MHz, CDCl₃) δ 168.80, 158.88, 146.42, 145.21, 136.79, 134.40, 129.98, 129.61, 128.31, 124.74; MS: Calcd. for $C_{12}H_6Cl_3NO$: 284.95. Found: 285 (M⁺), 250, 222, 187, 152; mp=106-111° C.

Example 25

4,5-Dichloro-6-(4-mehoxyphenyl)picolinoyl chloride

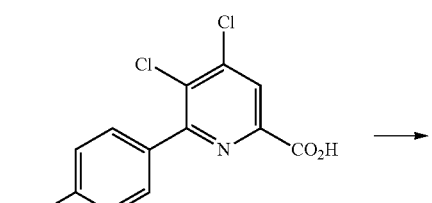

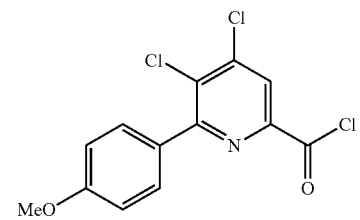

To a mixture of 4,5-dichloro-6-(4-methoxyphenyl)-picolinic acid (4.50 g, 15.1 mmol) in toluene (40 mL) was added thionyl chloride (1.65 mL, 22.6 mmol) and dimethylformamide (0.06 mL, 0.8 mmol). Reaction mixture was heated at 80° C. for 12 h. HPLC analysis of an aliquot of the reaction mixture treated with methanol and dimethylaminopyridine indicated complete conversion of the starting material. Reaction mixture was allowed to cool to room temperature and concentrated under reduced pressure to provide a yellow solid. Toluene (40 mL) was added to dissolve the solid and concentrated under reduced pressure and then this process was performed a second time. 4,5-Dichloro-6-(4-methoxyphenyl)-picolinoyl chloride was isolated as a yellow solid (4.64 g, 97% yield). ¹H NMR (400 MHz, CDCl₃) δ 8.09 (s, 1H), 7.85-7.77 (m, 2H), 7.06-6.98 (m, 2H); $^{13}$C NMR (101 MHz, CDCl$_3$) δ 168.91, 161.06, 158.35, 146.26, 145.13, 133.92, 131.35, 129.16, 124.13, 113.70; MS Calcd. for C$_{13}$H$_8$Cl$_3$NO$_2$: 314.96. Found: 253, 218.

Example 26

Isopropyl 4,5-difluoro-6-(4-chlorophenyl)picolinate

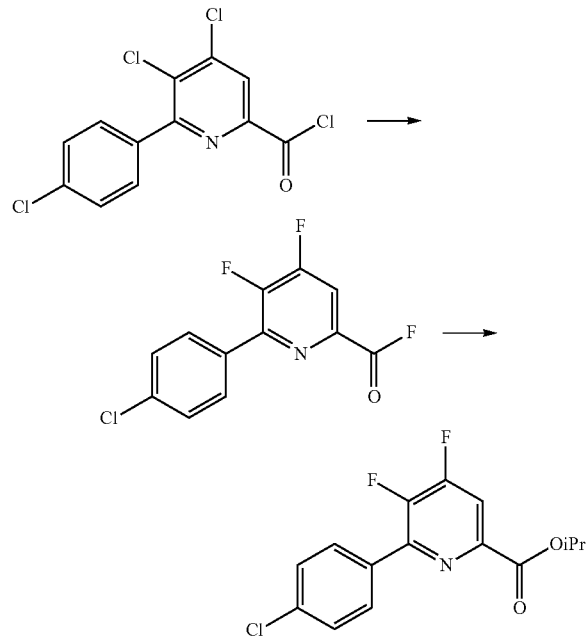

To a solution of 4,5-dichloro-6-(4-chlorophenyl)picolinoyl chloride (2.0 g, 6.23 mmol) in sulfolane (40 mL, dried over 4 Å molecular sieves, 100 ppm H$_2$O) was added potassium fluoride (2.2 g, 37.4 mmol). The reaction mixture was heated at 130° C. for 24 h. Reaction mixture was analyzed by GC-MS and $^{19}$F NMR. Data for 6-(4-chlorophenyl)-4,5-difluoropicolinoyl fluoride, GC-MS: m/z=271, 223; $^{19}$F NMR (376 MHz, Toluene-d$_8$) δ 17.05 (s), −123.81 (d, J=19.1 Hz), −140.17 (d, J=19.1 Hz). Reaction was allowed to cool to room temperature and triethylamine (1.1 mL, 7.8 mmol) and isopropanol (0.7 mL, 9.4 mmol) were added. After stirring for 1.5 h, the reaction mixture was diluted with water (100 mL) and transferred to a reparatory funnel. The reaction mixture was extracted with methyl tert-butyl ether (MTBE, 2×50 mL). The combined organic extracts were washed with water (3×50 mL) and saturated NaCl (50 mL) and concentrated under reduced pressure to provide a brown oil. The crude product oil was purified by silica gel flash chromatography (hexane/ethyl acetate gradient, 100% hexane→20% hexane/ethyl acetate) to provide 0.93 g (48% yield) of isopropyl 6-(4-chlorophenyl)-4,5-difluoropicolinate as a white solid. $^1$H NMR (400 MHz, CDCl$_3$) δ 8.04-7.98 (m, 2H), 7.90 (dd, J=9.4, 5.3 Hz, 1H), 7.51-7.45 (m, 2H), 5.31 (hept, J=6.3 Hz, 1H), 1.43 (d, J=6.3 Hz, 6H); $^{13}$C NMR (101 MHz, CDCl$_3$) δ 162.72 (d, J=3.5 Hz), 158.12 (d, J=12.6 Hz), 155.49 (d, J=12.4 Hz), 149.41 (d, J=11.0 Hz), 147.16 (dd, J=7.9, 1.0 Hz), 146.73 (d, J=10.9 Hz), 136.51 (d, J=0.9 Hz), 130.34 (d, J=6.6 Hz), 128.93 (s), 113.80 (d, J=16.1 Hz), 70.25 (s), 21.85 (s); $^{19}$F NMR (376 MHz, CDCl$_3$) δ −124.73 (dd, J=17.7, 9.5 Hz), −144.38 (dd, J=17.7, 5.4 Hz); MS Calcd. for C$_{16}$H$_{15}$F$_2$NO$_3$: 307.10. Found: 307 (M$^+$), 221, 206; mp=73-74° C.

Example 27

Isopropyl 4,5-difluoro-6-(phenyl)picolinate

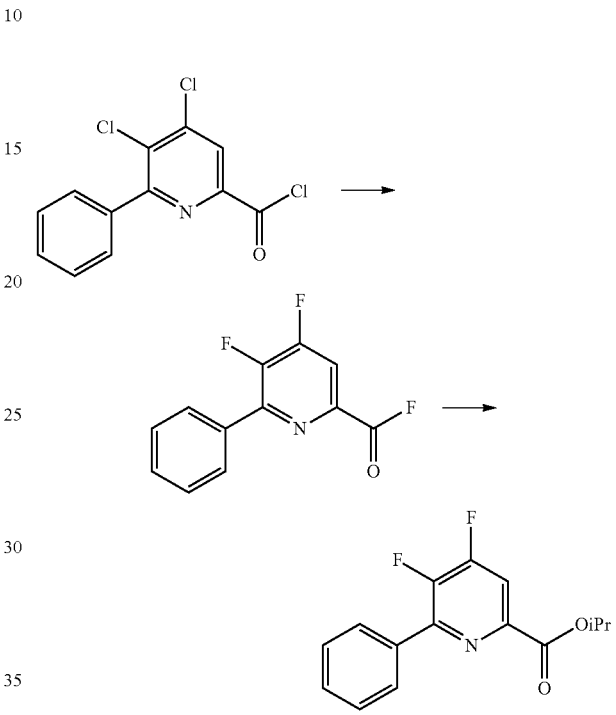

To a solution of 4,5-dichloro-6-phenylpicolinoyl chloride (1.76 g, 6.14 mmol) in sulfolane (40 mL, dried over 4 Å molecular sieves, ~100 ppm H$_2$O) was added potassium fluoride (2.14 g, 36.9 mmol). The reaction mixture was heated at 130° C. for 24 h. Reaction mixture was analyzed by GC-MS and $^{19}$F NMR. Data for 4,5-difluoro-6-phenylpicolinoyl fluoride, GC-MS: m/z=237, 189; $^{19}$F NMR (376 MHz, Toluene-d$_8$) δ 17.03 (s), −124.14 (d, J=19.1 Hz), −140.76 (d, J=19.1 Hz). Reaction was allowed to cool to room temperature and triethylamine (1.1 mL, 7.7 mmol) and isopropanol (0.7 mL, 9.2 mmol) were added. After stirring for 1.5 h, the reaction mixture was diluted with water (100 mL) and transferred to a reparatory funnel. The reaction mixture was extracted with methyl tert-butyl ether (MTBE, 2×50 mL). The combined organic extracts were washed with water (3×50 mL) and saturated NaCl (50 mL) and concentrated under reduced pressure to provide a brown oil. The crude product oil was purified by silica gel flash chromatography (hexane/ethyl acetate gradient, 100% hexane→20% hexane/ethyl acetate) to provide 1.2 g (70% yield) of isopropyl 4,5-difluoro-6-phenylpicolinate as a yellow oil. $^1$H NMR (400 MHz, CDCl$_3$) δ 8.07-7.99 (m, 2H), 7.89 (dd, J=9.4, 5.3 Hz, 1H), 7.56-7.42 (m, 3H), 5.31 (hept, J=6.3 Hz, 1H), 1.43 (d, J=6.3 Hz, 6H); $^{13}$C NMR (101 MHz, CDCl$_3$) δ 162.89 (d, J=3.4 Hz), 156.74 (dd, J=264.2, 12.5 Hz), 148.07 (dd, J=268.9, 10.8 Hz), 146.99 (dd, J=309.2, 10.8 Hz), 145.45 (s), 134.12-133.60 (m), 130.20 (s), 129.05 (d, J=5.9 Hz), 128.64 (s), 113.56 (d, J=16.0 Hz), 70.14 (s), 21.86 (s); $^{19}$F NMR (376 MHz, CDCl$_3$) δ −125.22 (dd, J=17.7, 9.5 Hz), −144.74 (dd, J=17.7, 5.4 Hz); MS Calcd. for $C_{15}H_{13}F_2NO_2$: 277.09. Found: 277 (M+), 218, 191.

Example 28

Isopropyl 4,5-difluoro-6-(4-methoxyphenyl)picolinate

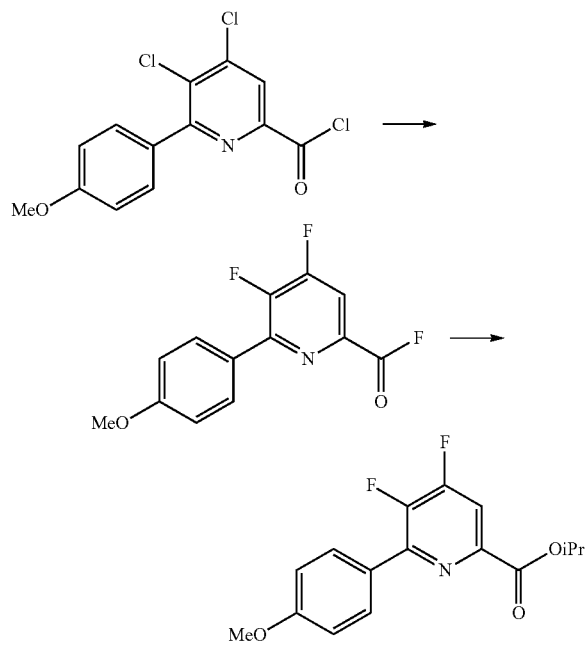

To a solution of 4,5-dichloro-6-(4-methoxyphenyl)picolinoyl chloride (2.5 g, 7.9 mmol) in sulfolane (40 mL, dried over 4 Å molecular sieves, 100 ppm of water) was added potassium fluoride (2.75 g, 47.4 mmol). The reaction mixture was heated at 150° C. for 24 h. Additional potassium fluoride (1.4 g, 24 mmol) was added, and reaction mixture was heated at 150° C. for an additional 24 h. Reaction mixture was analyzed by GC-MS and $^{19}$F NMR. Data for 4,5-difluoro-6-(4-methoxyphenyl)picolinoyl fluoride, GC-MS: m/z=267, 224, 176; $^{19}$F NMR (376 MHz, Tol) δ 16.94 (s), −124.65 (d, J=19.1 Hz), −141.23 (d, J=19.1 Hz). Reaction was allowed to cool to room temperature, and triethylamine (1.4 mL, 9.9 mmol) and isopropanol (0.9 mL, 11.9 mmol) were added. After stirring for 1.5 h, the reaction mixture was diluted with water (125 mL) and transferred to a reparatory funnel. The reaction mixture was extracted with methyl tert-butyl ether (MTBE, 2×75 mL). The combined organic extracts were washed with water (3×75 mL) and saturated NaCl (75 mL) and concentrated under reduced pressure to provide a brown oil. The crude product oil was purified by silica gel flash chromatography (hexane/ethyl acetate gradient, 100% hexane→20% hexane/ethyl acetate) to provide 0.60 g (25% yield) of isopropyl 4,5-difluoro-6-(4-methoxyphenyl)picolinate as a pale yellow solid. $^1$H NMR (400 MHz, CDCl$_3$) δ 8.08-8.01 (m, 2H), 7.82 (dd, J=9.5, 5.2 Hz, 1H), 7.04-6.97 (m, 2H), 5.30 (hept, J=6.3 Hz, 1H), 3.86 (s, 3H), 1.42 (d, J=6.3 Hz, 6H); $^{13}$C NMR (101 MHz, CDCl$_3$) δ 162.93 (s), 161.22 (s), 156.68 (d, J=263.5, 12.7 Hz), 147.70 (dd, J=267.9, 10.9 Hz), 146.61 (dd, J=286.4, 10.5 Hz), 145.18 (s), 130.53 (d, J=6.6 Hz), 126.43, 114.02 (s), 112.77 (d, J=16.1 Hz), 69.99 (s), 55.32 (s), 21.82 (s); $^{19}$F NMR (376 MHz, CDCl$_3$) δ −125.81 (d, J=17.7 Hz), −145.30 (d, J=19.1 Hz); MS Calcd. for $C_{16}H_{15}F_2NO_3$: 307.10. Found: 307 (M+), 221, 206.

Example 29

Isopropyl 4-amino-3-chloro-6-(4-chloro-2-fluoro-3-methoxyphenyl)-5-fluoropicolinate

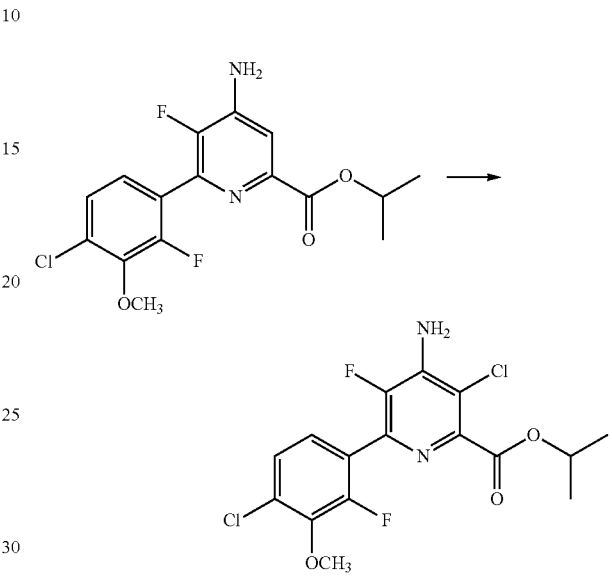

In a 50 mL three-neck round-bottomed flask was charged iso-propyl 4-(amino)-6-(4-chloro-2-fluoro-3-methoxyphenyl)-5-fluoropicolinate (450 mg, 1.26 mmol), acetonitrile (25 mL), and 1,3-dichloro-5,5-dimethylhyndantoin (137 mg, 0.69 mmol). The resulting mixture was sparged with N$_2$ for 5 min then heated to 68-70° C. After 2 h of stirring, an aliquot (1-2 μL) was taken and diluted with MeCN (2 mL). The aliquot was analyzed by HPLC by monitoring the consumption of starting material pyridyl ester. After the reaction was deemed complete the heating mantle was removed and the mixture was cooled to ambient temperature and was diluted with EtOAc (50 mL) and NaHSO$_3$ (20 mg) in H$_2$O (20 mL). The layers were then separated using a reparatory funnel. To the organic layer was added silica gel (10.1 g) and the solvent was removed using a rotary evaporator. The crude product on silica was then purified using a Combi-Flash silica gel purification gradient system EtOAc/Hex (5/100 to 70/30). Upon concentration a yellow solid weighing 466 mg (95%) was obtained. mp=113-115° C.; $^1$H NMR (400 MHz, DMSO-d$_6$) δ 7.47 (dd, J=8.8, 1.6 Hz, 1H), 7.29 (dd, J=8.4, 6.8 Hz, 1H), 7.07 (s, 2H), 5.17 (hept, J=6.0 Hz, 1H), 3.93 (s, 3H), 1.32 (d, J=6.0 Hz, 6H); $^{13}$C NMR (100.6 MHz, DMSO-d$_6$) δ 164.1, 154.3, 151.8 (d, J$_{F-C}$=3.7 Hz), 146.1, 145.5 (d, J$_{F-C}$=4.3 Hz), 143.8 (d, J$_{F-C}$=13.7 Hz), 143.5, 141.4 (d, J$_{F-C}$=14.2 Hz), 136.3 (d, J$_{F-C}$=13.4 Hz), 128.5 (d, J$_{F-C}$=3.1 Hz), 125.8 (d, J$_{F-C}$=2.6 Hz), 125.5 (d, J$_{F-C}$=3.4 Hz), 122.9 (dd, J$_{F-C}$=13.9, 3.8 Hz), 69.6, 61.6, 21.4; $^{19}$F {$^1$H} NMR (376.5 MHz, DMSO-d$_6$) δ −129.1 (d, J$_{F-F}$=27.9 Hz), −138.2 (d, J$_{F-F}$=27.9 Hz).

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:
1. A process for preparing a compound of Formula (I):

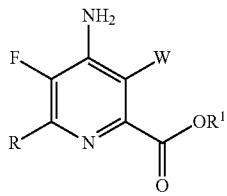

(I)

or a salt, solvate, isotopologue, or polymorph thereof, wherein:
W represents Cl, Br or I;
R represents $C_1$-$C_4$ alkyl, cyclopropyl, $C_2$-$C_4$ alkenyl or phenyl substituted with from 0 to 5 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; comprising:
(a) fluorinating a compound of Formula (II):

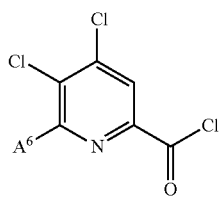

(II)

wherein $A^6$ is halogen or R;
with a source of fluoride ion to form a compound of Formula (III):

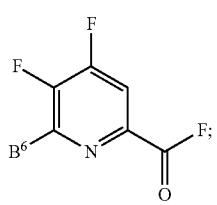

(III)

wherein $B^6$ is F or R;
and transforming the compound of Formula (III) to a compound of Formula (IV):

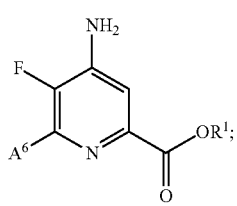

(IV)

(b) halogenating a compound of Formula (IV) with a halogen source to form a compound of Formula (V):

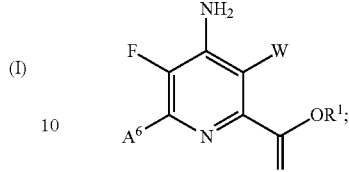

(V)

and
(c) coupling a compound of Formula (VI)

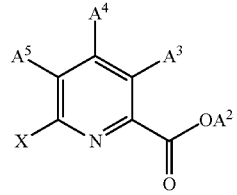

(VI)

wherein
X is Cl, Br, or I;
$A^2$ is hydrogen or $R^1$;
$A^3$ is hydrogen or W;
$A^4$ is Cl, F, $NH_2$, $NHCOCH_3$, or a protected amino group;
$A^5$ is F or Cl;
with a compound of Formula (VII)

R-Met (VII)

wherein Met is Zn-halide, Zn—R, tri-($C_1$-$C_4$ alkyl)tin, copper, or $B(OR^2)(OR^3)$, where $R^2$ and $R^3$ are each independently, hydrogen, $C_1$-$C_4$ alkyl, or when taken together form an ethylene or propylene group;
in the presence of a transition metal catalyst to form a compound of Formula (VIII):

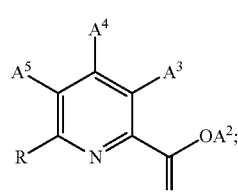

(VIII)

wherein transformation (c) may occur prior to, between, or after transformations (a) and (b).

2. The process of claim 1, wherein R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy.

3. The process of claim 1, wherein the transformation of a compound of Formula (III) to a compound of Formula (IV) comprises:
contacting the compound of Formula (III) with an alcohol $R^1OH$ to form a compound of Formula (IX):

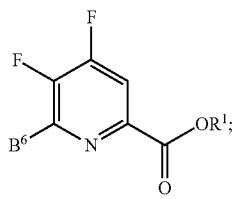

(IX)

and aminating the compound of Formula (IX) with an ammonia source to form the compound of Formula (IV).

4. The process of claim 1, wherein the transformation of a compound of Formula (III) to a compound of Formula (IV) comprises:

contacting the compound of Formula (III) with an ammonia source to form a compound of Formula (X):

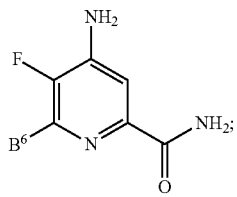

(X)

and contacting the compound of Formula (X) with an acid HX and an alcohol $R^1OH$ to form the compound of Formula (IV), wherein X is I, Br, or Cl.

5. The process of claim 1, comprising:

transformation (a), which comprises:

(a-1) fluorinating a compound of Formula (A):

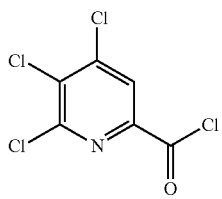

(A)

with a source of fluoride ion to form a compound of Formula (B):

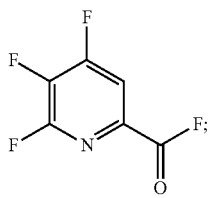

(B)

(a-2) contacting the compound of Formula (B) with an alcohol $R^1OH$ to form a compound of Formula (C):

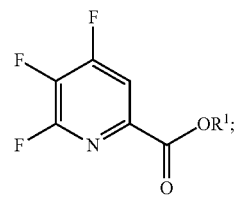

(C)

(a-3) aminating the compound of Formula (C) with an ammonia source to form a compound of Formula (D):

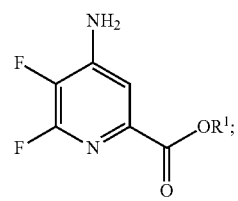

(D)

and (a-4) contacting the compound of Formula (D) with an iodide, bromide or chloride source under conditions suitable for halogen exchange to form a compound of Formula (E):

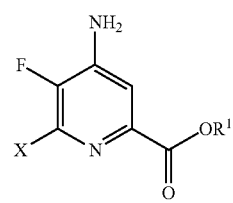

(E)

wherein X is Cl, Br, or I;

transformation (c), which comprises:

coupling the compound of Formula (E) with a compound of Formula (F)

R—Met (F)

wherein Met is Zn-halide, Zn—R, tri-($C_1$-$C_4$ alkyl)tin, copper, or B($OR^2$)($OR^3$), where $R^2$ and $R^3$ are each independently, hydrogen, $C_1$-$C_4$ alkyl, or when taken together form an ethylene or propylene group;

in the presence of a transition metal catalyst to form a compound of Formula (G):

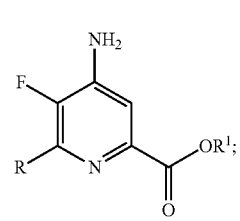

(G)

and transformation (b), which comprises:
halogenating the compound of Formula (G) with a halogen source to form a compound of Formula (I).

6. The process of claim 1, comprising:
transformation (a), which comprises:
(a-1) fluorinating a compound of Formula (A):

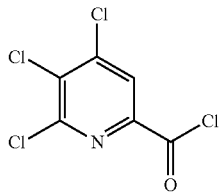
(A)

with a source of fluoride ion to form a compound of Formula (B):

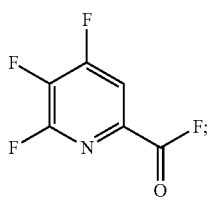
(B)

(a-2) contacting the compound of Formula (B) with an alcohol $R^1OH$ to form a compound of Formula (C):

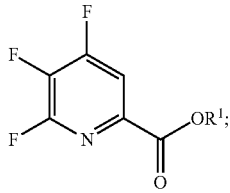
(C)

(a-3) aminating the compound of Formula (C) with an ammonia source to form a compound of Formula (D):

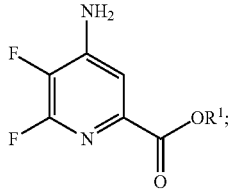
(D)

and
(a-4) contacting the compound of Formula (D) with an iodide, bromide or chloride source under conditions suitable for halogen exchange to form a compound of Formula (E):

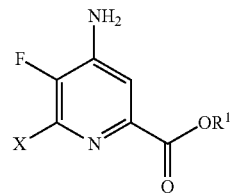
(E)

wherein X is Cl, Br, or I;
transformation (b), which comprises:
halogenating the compound of Formula (E) with a halogen source to form a compound of Formula (H):

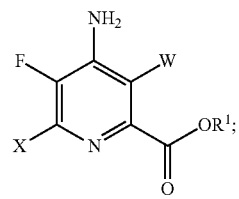
(H)

and
transformation (c), which comprises:
coupling the compound of Formula (H) with a compound of Formula (F)

R-Met (F)

wherein Met is Zn-halide, Zn—R, tri-($C_1$-$C_4$ alkyl)tin, copper, or $B(OR^2)(OR^3)$, where $R^2$ and $R^3$ are each independently, hydrogen, $C_1$-$C_4$ alkyl, or when taken together form an ethylene or propylene group;
in the presence of a transition metal catalyst to form a compound of Formula (I).

7. The process of claim 1, comprising:
transformation (c), which comprises:
coupling a compound of Formula (J):

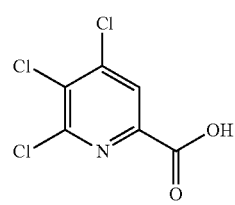
(J)

with a compound of Formula (F)

R-Met (F)

wherein Met is Zn-halide, Zn—R, tri-($C_1$-$C_4$ alkyl)tin, copper, or $B(OR^2)(OR^3)$, where $R^2$ and $R^3$ are each independently, hydrogen, $C_1$-$C_4$ alkyl, or when taken together form an ethylene or propylene group;
in the presence of a transition metal catalyst to form a compound of Formula (K):

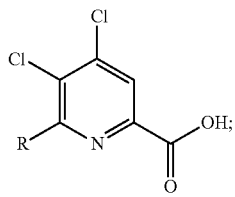
(K)

transformation (a), which comprises:
(a-1) transforming the compound of Formula (K) to a compound of Formula (L):

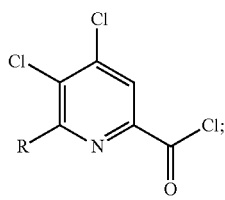
(L)

under conditions suitable for the formation of acid chloride;
(a-2) fluorinating the compound of Formula (L) with a source of fluoride ion to form a compound of Formula (M):

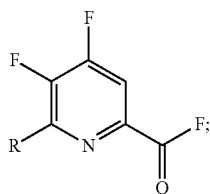
(M)

(a-3) contacting the compound of Formula (M) with an alcohol $R^1OH$ to form a compound of Formula (N):

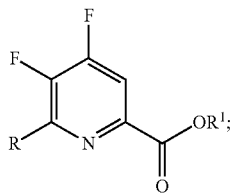
(N)

and
(a-4) aminating the compound of Formula (N) with an ammonia source to form a compound of Formula (O):

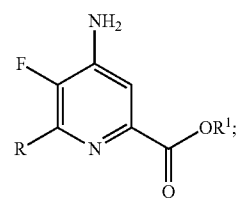
(O)

and
transformation (b), which comprises:
halogenating the compound of Formula (O) with a halogen source to form a compound of Formula (I).
8. The process of claim 1, comprising:
transformation (c), which comprises:
(c-1) coupling a compound of Formula (P):

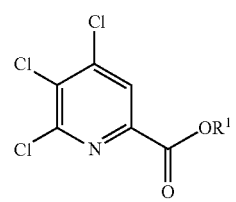
(P)

with a compound of Formula (F)

R-Met  (F)

wherein Met is Zn-halide, Zn—R, tri-($C_1$-$C_4$ alkyl)tin, copper, or $B(OR^2)(OR^3)$, where $R^2$ and $R^3$ are each independently, hydrogen, $C_1$-$C_4$ alkyl, or when taken together form an ethylene or propylene group;
in the presence of a transition metal catalyst to form a compound of Formula (Q):

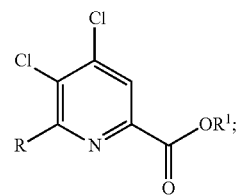
(Q)

and
(c-2) hydrolyzing the compound of Formula (Q) to a compound of Formula (K):

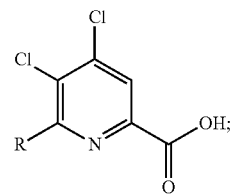
(K)

transformation (a), which comprises:
(a-1) transforming the compound of Formula (K) to a compound of Formula (L):

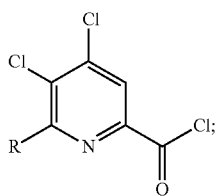

(L)

under conditions suitable for the formation of acid chloride;

(a-2) fluorinating the compound of Formula (L) with a source of fluoride ion to form a compound of Formula (M):

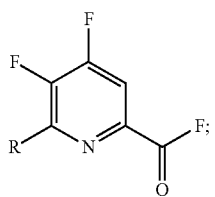

(M)

(a-3) contacting the compound of Formula (M) with a compound R¹OH to form a compound of Formula (N):

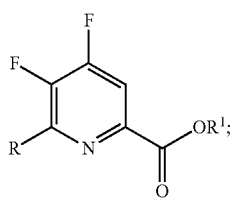

(N)

and (a-4) aminating the compound of Formula (N) with an ammonia source to form a compound of Formula (O):

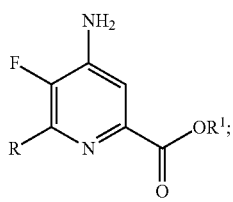

(O)

and transformation (b), which comprises:

halogenating the compound of Formula (O) with a halogen source to form a compound of Formula (I).

9. The process of claim 1, further comprising protecting the NH$_2$ substituent in the 4-position of the pyridine structure prior to transformation (c); and further comprising a deprotecting step.

10. The process of claim 1, wherein R is phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy.

11. The process of claim 1, wherein an amine-containing compound of Formulas (I), (IV), (V), (VI), or (VIII) is purified by: a) protonating with an acid to form a salt, b) isolating the salt in higher purity by crystallization, precipitation or extraction, and c) neutralizing the purified salt with a base to form the purified neutral amine-containing product or intermediate.

12. The process of claim 1, wherein the source of fluoride ion is a metal fluoride.

13. The process of claim 12, wherein the metal fluoride is selected from sodium fluoride, potassium fluoride and cesium fluoride.

14. The process of claim 13, wherein the metal fluoride is potassium fluoride.

15. The process of claim 1, wherein the fluorination step in transformation (a) occurs in the presence of a catalyst selected from a crown ether, a phosphonium halide, a polyether, a phosphazenium salt, and a tetra-substituted ammonium halide.

16. The process of claim 15, wherein the catalyst is a crown ether.

17. The process of claim 16, wherein the crown ether is 18-crown-6.

18. The process of claim 1, wherein the fluorination step in transformation (a) occurs in the presence of a solvent selected from an alkyl nitrile or an alkyl sulfone.

19. The process of claim 18, wherein the solvent is acetonitrile or sulfolane.

20. The process of claim 1, wherein the solvate is a hydrate.

* * * * *